United States Patent von Sprecher et al.

[11] Patent Number: 5,508,408
[45] Date of Patent: Apr. 16, 1996

[54] QUINOLINE COMPOUND

[75] Inventors: Andreas von Sprecher, Oberwil, Switzerland; Andreas Beck, Freiburg, Germany; Marc Gerspacher, Brugg, Switzerland

[73] Assignee: Ciba-Geigy Corporation, Tarrytown, N.Y.

[21] Appl. No.: 288,537

[22] Filed: Aug. 10, 1994

[30] Foreign Application Priority Data

Sep. 10, 1993 [DE] Germany ............................ 93810645.7

[51] Int. Cl.$^6$ ...................... C07D 215/06; C07D 221/16; C07D 221/08
[52] U.S. Cl. .................. 546/175; 546/79; 546/93; 546/101
[58] Field of Search ................. 546/175, 79, 93, 546/101, 175; 514/311

[56] References Cited

U.S. PATENT DOCUMENTS

| | | | |
|---|---|---|---|
| 4,749,701 | 6/1988 | Hayashi | 514/247 |
| 4,826,987 | 5/1989 | Nielson et al. | 546/174 |
| 4,902,700 | 2/1990 | Hayasi et al. | 514/365 |
| 4,925,861 | 5/1990 | Hayashi | 514/367 |
| 4,962,203 | 10/1990 | Young et al. | 546/180 |
| 5,109,009 | 4/1992 | Nielson et al. | 514/311 |
| 5,157,039 | 10/1992 | Nielson et al. | 514/311 |

FOREIGN PATENT DOCUMENTS

| | | |
|---|---|---|
| 0219308 | 4/1987 | European Pat. Off. . |
| 0219307 | 4/1987 | European Pat. Off. . |
| 0228959 | 7/1987 | European Pat. Off. . |
| 0355353 | 2/1990 | European Pat. Off. . |

OTHER PUBLICATIONS

Sawyer et al "Optimization of the Quinoline and Substituted Benzyl Moieties of a Series of Phenyl-tetrazole Leukotriene D$_4$ Receptor Antagonists'" J. Med Chem 1992 vol. 35 (1200–1209).

Musser et al. "Leukotriene D$_4$ Antagonists and 5–Lipoxygenase Inhibitors. Synthesis of Benzoheterocyclic [(Methoxyphenyl)Amino] oxoalkanoic Acid Esters" J. Med. Chem. 1987 vol. 30 (400–405).

Musser et al "Synthesis of [[(Naphthalenylmethoxy)– and [[(Quinolinylmethoxy)phenyl]amino]oxoalkanoic Acid Esters. A Novel Series of Leokotriene D$_4$ Antagonists and 5–Lipoxygenase Inhibitors" J. Med. Chem. 1986 vol. 29 (1429–1435).

Musser et al "5–Lipoxygenase: Properties, Pharmacology and the Quinolinyl(bridged)aryl Class of Inhibitors" Journal of Medicinal Chemistry, vol. 35 (2501–2524) 1992.

Labaudiniere et al "w–[(4–Phenyl-2–Quinolyl)oxyl]alkanoic Acid Derivatives; A New Family of Potent L7B$_4$ Antagonists" J. Med. Chem (1992) vol. 35 (4306–4314).

Musser, John, "Leukotriene D4 Antagonists . . . ", J Med CHem, 30(2), pp. 400–405, 1987.

Musser, John, "Synthesis of . . . ", J Med Chem, 29(8), pp. 1429–1435, 1986.

Chemical Abstracts 110:186646, 1989.
Chemical Abstracts 109: 403, 1988.
Chemical Abstracts 106: 102166, 1987.
Chemical Abstracts 105: 97289, 1986.

Primary Examiner—C. Warren Ivy
Assistant Examiner—D. Margaret M. Mach
Attorney, Agent, or Firm—Irving M. Fishman; Karen G. Kaiser

[57] ABSTRACT

Compounds of formula I

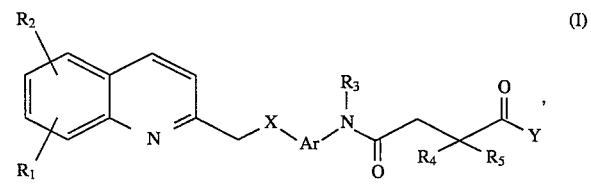

wherein $R_1$–$R_5$, X, Ar and Y are as defined in the description, have valuable pharmaceutical properties and are especially effective as leukotriene antagonists. They are prepared in a manner known per se.

13 Claims, No Drawings

QUINOLINE COMPOUND

The invention relates to compounds of formula I

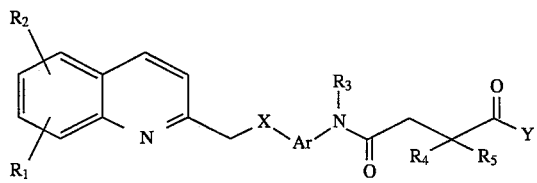

wherein $R_1$ and $R_2$ are each independently of the other hydrogen, lower alkyl, halo-lower alkyl, aryl-lower alkyl, cycloalkyl, halogen, hydroxy, lower alkoxy, halo-lower alkoxy, aryl-lower alkoxy, acyloxy, mercapto, lower alkyl(-thio, -sulfinyl or -sulfonyl), amino, lower alkylamino, di-lower alkylamino, acylamino, nitro, acyl, carboxy, lower alkoxycarbonyl, aminocarbonyl, N-lower alkylaminocarbonyl, N,N-di-lower alkylaminocarbonyl or cyano, or $R_1$ and $R_2$ together form —$(CH_2)_m$—, wherein m is 3, 4 or 5, $R_3$ is hydrogen, lower alkyl, (carboxy-, lower alkoxycarbonyl-, aminocarbonyl-, N-lower alkylaminocarbonyl-, N,N-di-lower alkylaminocarbonyl- or cyano-)lower alkyl, phenyl-lower alkyl; (carboxy-, lower alkoxycarbonyl-, aminocarbonyl-, N-lower alkylaminocarbonyl-, N,N-di-lower alkylaminocarbonyl- or cyano-)phenyl-lower alkyl, which may be additionally substituted in the phenyl ring by lower alkoxy; or lower alkyl that is substituted by the group —$NHSO_2R$, wherein R is lower alkyl, halo-lower alkyl or aryl, $R_4$ and $R_5$ are each independently of the other lower alkyl, or $R_4$ and $R_5$ together form —$(CH_2)_n$—, wherein n is 3, 4, 5 or 6, X is O, S, SO or $SO_2$, Ar is 1,3-phenylene or 2,7-naphthylene, and Y is hydroxy, lower alkoxy, amino, lower alkylamino or di-lower alkylamino;

and to salts thereof, to processes for the preparation of those compounds, to pharmaceutical compositions that comprise those compounds, and to the use of those compounds in the therapeutic treatment of the human or animal body or in the preparation of pharmaceutical compositions.

Within the scope of the present Application, the general terms used hereinbefore and hereinafter have preferably the following meanings:

The term "lower" denotes a radical having up to and including 7 and especially up to and including 4 carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

$C_1$–$C_3$alkyl is methyl, ethyl, n-propyl or isopropyl.

Lower alkyl as a meaning of $R_4$ and $R_5$ is preferably ethyl.

Halo-lower alkyl is, for example, trifluoromethyl.

Halo-lower alkoxy is, for example, trifluoromethoxy.

Cycloalkyl is preferably $C_3$–$C_8$- and especially $C_5$–$C_6$-cycloalkyl, which is intended to mean that it contains from 3 to 8 and 5 or 6 ring carbon atoms, respectively. Cycloalkyl may, however, also be substituted, for example by lower alkyl.

Halogen is especially chlorine or bromine, or more especially fluorine, but may also be iodine.

Acyl is, for example, lower alkanoyl; lower alkanoyl is, for example, acetyl, propionyl or pivaloyl, but also, for example, formyl.

Aminocarbonyl is the group —$CONH_2$.

If $R_1$ and $R_2$ together form the bivalent radical —$(CH_2)_m$—, then that bivalent radical is preferably linked to two vicinal carbon atoms of the phenyl ring (for example as 6,7-cyclopentanoquinolinyl).

If $R_4$ and $R_5$ together form the bivalent radical —$(CH_2)_n$—, then that bivalent radical is linked twice to the same carbon atom so that a cycloalkane is formed.

Aryl is, for example, phenyl that is unsubstituted or substituted. Aryl is preferably phenyl that is unsubstituted or substituted by one or more, especially one or two, substituents from the group consisting of lower alkyl, lower alkoxy, lower alkenyloxy, hydroxy, lower alkanoyloxy, nitro, amino, halogen, trifluoromethyl, carboxy, lower alkoxycarbonyl, aminocarbonyl, N-lower alkylaminocarbonyl, N,N-di-lower alkylaminocarbonyl, cyano, lower alkanoyl, benzoyl and lower alkylsulfonyl. Aryl is especially phenyl that is unsubstituted or substituted by lower alkyl, lower alkoxy, lower alkenyloxy, hydroxy, halogen or by trifluoromethyl, and is more especially phenyl.

1,3-phenylene and 2,7-naphthylene are the bivalent radicals

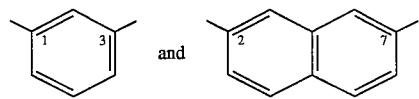

Salts of compounds of formula I are especially pharmaceutically acceptable salts, more especially salts with bases, such as corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-lower alkylamines, such as hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable as mono-lower alkylamines are, for example, ethyl- and t-butyl-amine, as di-lower alkylamines, for example, diethyl- and diisopropyl-amine and as tri-lower alkylamines, for example, trimethyl- and triethyl-amine. Corresponding hydroxy-lower alkylamines are, for example, mono-, di- and tri-ethanolamine; hydroxy-lower alkyl-lower alkylamines are, for example, N,N-dimethylamino- and N,N-diethylamino-ethanol; suitable as polyhydroxy-lower alkylamine is, for example, glucosamine. In certain cases, acid addition salts may also be formed, for example with strong inorganic acids, such as mineral acids, for example sulfuric acid, a phosphoric acid or a hydrohalic acid, with strong organic carboxylic acids, such as lower alkanecarboxylic acids, for example acetic acid, such as saturated or unsaturated dicarboxylic acids, for example malonic, maleic or fumaric acid, or such as hydroxycarboxylic acids, for example tartaric acid or citric acid, or with sulfonic acids, such as lower alkane- or unsubstituted or substituted benzene-sulfonic acids, for example methane- or p-toluene-sulfonic acid. Compounds of formula I having an acidic group, for example carboxy, and a basic group, for example amino, may, for example, also be in the form of internal salts, that is to say in zwitterionic form, or one part of the molecule may be in the form of an internal salt and another part may be in the form of a normal salt. Salts that are not suitable for pharmaceutical uses are also included since they can be used, for example, for the isolation or purification of free compounds I and the pharmaceutically acceptable salts thereof.

The compounds of formula I have valuable pharmacological properties, especially a pronounced antagonistic activity in respect of leukotrienes.

For example, in vitro with an $IC_{50}$ value of from approximately 0.0001 to approximately 0.05 μmol/l, they inhibit the contraction of the small intestine of the guinea pig induced by leukotriene $D_4$ ($LTD_4$). That activity, which is referred to as $LTD_4$-antagonism, can be verified experimentally, for example, by inducing contractions in guinea pig ileum segments in an organ bath [standard method: Tyrode's solution at 38° C. while gassing with oxicarbon (mixture of oxygen and carbon dioxide) at a load of 1 g] using synthetic leukotriene $D_4$ (in the form of the potassium salt) and recording those contractions isotonically. The degree of inhibition of the contractions by the test compound is determined in the form of $IC_{50}$ values after 2 minutes' pre-incubation, the $IC_{50}$ being the concentration at which the test contractions are reduced by 50%.

The compounds of formula I also exhibit excellent activity in vivo. For example, in the bronchial spasm standard test on guinea pigs, after the administration of the test compound in the form of an aerosol a pronounced antagonistic effect in respect of $LTD_4$ is observed ($ED_{50}$ from approximately 0.0003 to approximately 0.05% w/v spray/min). In that test model, narcotised guinea pigs (urethane 1.4 g/kg) are installed in a plethysmograph. Oesophagal pressure and respiratory flow are converted with appropriate computer support into various pulmonary parameters, for example compliance. After a brief stabilisation phase, the test compound is administered using a Monaghan ultrasound spray device. The aerosol produced (vehicle or active ingredient) is inhaled for 1 minute by the spontaneously breathing animals via a tracheal cannula. After a specific treatment time has elapsed, $LTD_4$ is administered for 2 minutes using a second, identical inhalation system. The reduction in compliance serves as a measure of the severity of the bronchial constriction induced by $LTD_4$. The average values of the treatment group are compared with the average values of the control animals. The activity of the test compound is calculated in accordance with the following formula:

$$\% \text{ inhib.} = 100 - \frac{(100 - \text{compliance composition}) \cdot 100}{(100 - \text{compliance control})}$$

and the $IC_{50}$ values are determined by linear regression analysis.

The compounds of formula I are particularly effective when administered orally, being distinguished by a high degree of efficacy and a long duration of efficacy. For example, the test compounds are administered to the animals in the form of a suspension in methylcellulose by means of a stomach tube, using the same experimental procedure as described above in the bronchial spasm standard test. With treatment times of up to 8 hours, a marked reduction in the bronchial constriction produced by $LTD_4$ is observed in the range of approximately from 0.003 to 1.0 mg/kg.

The compounds of formula I also exhibit excellent effects in the case of bronchial spasm induced by leukotriene $E_4$ ($LTE_4$), for example when they are administered orally. With treatment times of up to 8 hours, strong activity is again observed in the range of approximately from 0.001 to 1.0 mg/kg p.o.

The compounds of formula I can therefore be used therapeutically, for example, in all cases where the activity of leukotrienes gives rise to pathological conditions, the compounds of formula I alleviating or eliminating those conditions. Leukotrienes play an important role, inter alia, in the occurrence of allergic and inflammatory processes. Accordingly, the compounds of formula I can be used, for example, as anti-allergic drugs, for example in the treatment of allergic conditions and disorders, such as, especially, asthma, but also, for example, hay fever or obstructive lung diseases. The compounds of formula I can also be used, for example, in the treatment of inflammatory diseases of the lungs and other organs, for example cystic fibrosis or adult respiratory distress syndrome, and also, for example, psoriasis, Colitis ulcerosa, Crohn's disease, septic shock or inflammatory diseases of the eye.

The invention relates especially to the compounds of formula I wherein $R_1$ and $R_2$ are each independently of the other hydrogen, lower alkyl, halo-lower alkyl, aryl-lower alkyl, cycloalkyl, halogen, hydroxy, lower alkoxy, aryl-lower alkoxy, acyloxy, mercapto, lower alkyl(-thio, -sulfinyl or -sulfonyl), amino, lower alkylamino, di-lower alkylamino; acylamino, nitro, acyl, carboxy, lower alkoxycarbonyl, aminocarbonyl, N-lower alkylaminocarbonyl, N,N-di-lower alkylaminocarbonyl or cyano, $R_3$ is hydrogen, lower alkyl, (carboxy-, lower alkoxycarbonyl-, aminocarbonyl-, N-lower alkylaminocarbonyl-, N,N-di-lower alkylaminocarbonyl- or cyano-)lower alkyl, phenyl-lower alkyl, (carboxy-, lower alkoxycarbonyl-, aminocarbonyl-, N-lower alkylaminocarbonyl-, N,N-di-lower alkylaminocarbonyl- or cyano-)phenyl-lower alkyl, or lower alkyl that is substituted by the group —$NHSO_2R$, wherein R is lower alkyl, halo-lower alkyl or aryl, $R_4$ and $R_5$ are each independently of the other lower alkyl, or $R_4$ and $R_5$ together form —$(CH_2)_4$— or —$(CH_2)_5$—, X is O, S, SO or $SO_2$, Ar is 1,3-phenylene or 2,7-naphthylene, and Y is hydroxy, lower alkoxy, amino, lower alkylamino or di-lower alkylamino; and to salts thereof.

The invention relates preferably to the compounds of formula I wherein $R_1$ and $R_2$ are each independently of the other hydrogen, lower alkyl, halo-lower alkyl, phenyl-lower alkyl, halogen, hydroxy, lower alkoxy, halo-lower alkoxy, phenyl-lower alkoxy, lower alkyl(-thio, -sulfinyl or -sulfonyl), nitro, lower alkanoyl or cyano, or $R_1$ and $R_2$ together form —$(CH_2)_3$— or —$(CH_2)_4$—, $R_3$ is hydrogen, lower alkyl, carboxy-lower alkyl, lower alkoxycarbonyl-lower alkyl, N,N-di-lower alkylaminocarbonyl-lower alkyl; (carboxy- or lower alkoxycarbonyl-)-phenyl-lower alkyl, which may be additionally substituted in the phenyl ring by lower alkoxy; or lower alkyl that is substituted by the group —$NHSO_2R$, wherein R is lower alkyl, trifluoromethyl, phenyl, lower alkyl-phenyl or lower alkenyloxy-phenyl, $R_4$ and $R_5$ are each independently of the other lower alkyl, or $R_4$ and $R_5$ together form —$(CH_2)_4$— or —$(CH_2)_5$—, X is O, S, SO or $SO_2$, Ar is 1,3-phenylene or 2,7-naphthylene, and Y is hydroxy, lower alkoxy, amino, lower alkylamino or di-lower alkylamino; and to salts thereof.

The invention relates preferably to the compounds of formula I wherein $R_1$ and $R_2$ are each independently of the other hydrogen, lower alkyl, trifluoromethyl, halogen, lower alkoxy, lower alkyl(-thio, -sulfinyl or -sulfonyl), nitro or cyano, $R_3$ is hydrogen, lower alkyl, carboxy-lower alkyl, lower alkoxycarbonyl-lower alkyl, N,N-di-lower alkylaminocarbonyl-lower alkyl or (carboxy- or lower alkoxycarbonyl-)-phenyl-lower alkyl, $R_4$ and $R_5$ are each independently of the other lower alkyl, or $R_4$ and $R_5$ together form $-(CH_2)_4-$ or $-(CH_2)_5-$, X is O, S, SO or $SO_2$, Ar is 1,3-phenylene or 2,7-naphthylene, and Y is hydroxy, lower alkoxy, amino, lower alkylamino or di-lower alkylamino; and to salts thereof.

The invention relates more especially to the compounds of formula I wherein $R_1$ and $R_2$ are each independently of the other hydrogen, lower alkyl, trifluoromethyl, halogen, lower alkoxy, lower alkylthio, nitro or cyano, $R_3$ is hydrogen, lower alkyl, carboxy-lower alkyl or carboxyphenyl-lower alkyl, $R_4$ and $R_5$ are each independently of the other lower alkyl, or $R_4$ and $R_5$ together form $-(CH_2)_4-$ or $-(CH_2)_5-$, X is O, S, SO or $SO_2$, Ar is 1,3-phenylene or 2,7-naphthylene, and Y is hydroxy, lower alkoxy or amino, and to salts thereof.

The invention relates more especially to the compounds of formula I wherein $R_1$ is hydrogen, lower alkyl, trifluoromethyl, halogen, lower alkoxy, lower alkylthio, nitro or cyano, $R_2$ and $R_3$ are hydrogen, $R_4$ and $R_5$ are each independently of the other $C_1$-$C_3$alkyl, or $R_4$ and $R_5$ together form $-(CH_2)_4-$ or $-(CH_2)_5-$, X is O or S, Ar is 1,3-phenylene or 2,7-naphthylene, and Y is hydroxy, and to pharmaceutically acceptable salts thereof.

An especially preferred group among the compounds of formula I comprises the compounds of formula Ia

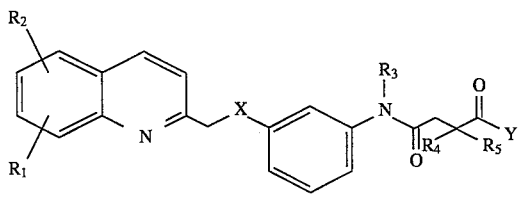

wherein $R_1$ and $R_2$ are each independently of the other hydrogen, chlorine or fluorine, $R_3$ is hydrogen, $R_4$ and $R_5$ are ethyl, X is O, and Y is hydroxy, lower alkoxy or amino, and pharmaceutically acceptable salts thereof.

Especially preferred are the compounds of formula Ia wherein $R_1$ is hydrogen, chlorine or fluorine, $R_2$ is hydrogen or fluorine, $R_3$ is hydrogen, $R_4$ and $R_5$ are ethyl, X is O, and Y is hydroxy, and pharmaceutically acceptable salts thereof.

The invention relates especially to the specific compounds described in the Examples and to salts thereof.

The compounds of formula I can be prepared in a manner known per se, for example as follows:

(a) a compound of formula II

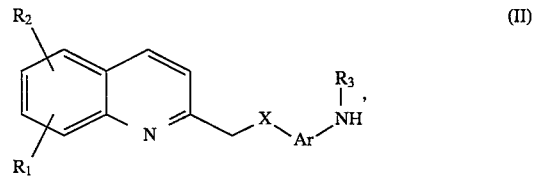

wherein $R_1$, $R_2$, $R_3$, X and Ar are as defined for formula I, is reacted with a compound of formula III

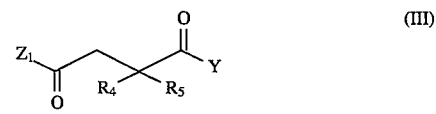

wherein the group $-COZ_1$ is carboxy or a reactive carboxy derivative and $R_4$, $R_5$ and Y are as defined for formula I, or (b) a compound of formula IV

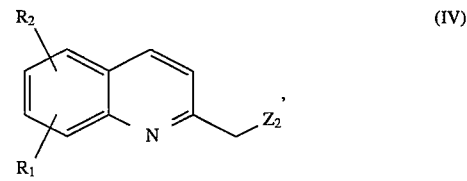

wherein $Z_2$ is a nucleofugal leaving group and $R_1$ and $R_2$ are as defined for formula I, is reacted with a compound of formula V

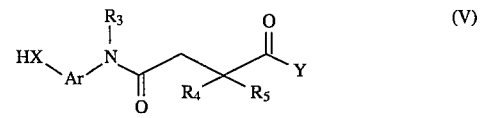

wherein $R_3$, $R_4$, $R_5$, X, Ar and Y are as defined for formula I, or with a salt thereof, and, if desired, an obtainable compound of formula I is converted into a different compound of formula I, and/or, if desired, an obtainable salt is converted into the free compound or into a different salt, and/or, if desired, an obtainable free compound of formula I having salt-forming properties is converted into a salt.

Process (a): The reaction according to process (a) corresponds to the acylation known per se of primary or secondary aromatic amines.

A reactive carboxy derivative $-COZ_1$ is, for example, a carboxylic acid halide, for example an acid chloride, a carboxylic acid imidazolide, a carboxylic acid anhydride or a reactive carboxylic acid ester, for example a p-nitrophenyl ester.

For the preparation of compounds of formula I wherein Y=OH, it is also advantageously possible to use an internal acid anhydride as the compound of formula III; such an internal acid anhydride corresponds to a compound of formula III wherein the radicals $Z_1$ and Y together form an $-O-$ bridge. It can be produced from the corresponding dicarboxylic acid by reaction with, for example, oxalyl chloride or acetyl chloride.

An advantageous method of preparing compounds of formula I wherein Y=lower alkoxy, especially also those having a voluminous radical $R_3$ ($R_3$=lower alkyl or substituted lower alkyl), comprises reacting a compound of formula II with a compound of formula III, wherein Y is lower alkoxy and $Z_1$ is carboxy, (semiester) in the presence of, for example, N-(3-dimethylaminopropyl)-N'-ethylcarbodiimide hydrochloride and 4-dimethylaminopyridine.

The compounds of formula II wherein X is O or S are prepared, for example, by reacting a compound of formula IV [see Process (b)] with a compound of formula VI

(VI)

wherein X is O or S. Compounds of formula II wherein X is SO or $SO_2$ are advantageously obtained by the controlled oxidation of the corresponding compounds of formula II wherein X is S, for example using equimolar amounts or an excess of organic peracids, such as meta-chloroperbenzoic acid, or peroxides, for example tert-butyl hydroperoxide or cumene hydroperoxide.

The oxidation to the sulfoxide (X=SO) can also be carried out enantioselectively, for example using chiral titanium complexes, for example using Ti(O-isopropyl)$_4$/tartaric acid diethyl ester/water.

The compounds of formula III are known per se or are prepared analogously to the known compounds.

Process (b): Process (b) is used preferably for the preparation of compounds of formula I wherein X is O or S. A hydroxy- or mercapto-aryl compound of formula V is alkylated in a manner known per se with a quinolinemethyl derivative of formula IV.

In a compound of formula IV the nucleofugal leaving group $Z_2$ is, for example, halogen, especially bromine, iodine or chlorine, or sulfonyloxy, for example methyl- or p-toluenesulfonyloxy.

The compounds of formula IV are prepared in a manner known per se, for example from the corresponding methylquinolines, for example by halogenation, for example using N-bromosuccinimide.

The compounds of formula V are prepared, for example, analogously to the compounds of formula I in Process (a), a compound of formula VI [see Process (a)] being used as starting material instead of a compound of formula II.

Compounds of formula I can also be converted into different compounds of formula I.

For example, a compound of formula I wherein $R_3$ is hydrogen can be alkylated at the amide nitrogen to give a compound of formula I wherein $R_3$ is lower alkyl or substituted lower alkyl. The reaction is carried out in the presence of a suitable base, for example NaH or sodium methoxide, using as the alkylating agent, for example, a compound $R_3$-$Z_3$, wherein $Z_3$ is a nucleofugal leaving group, for example halogen, especially bromine, iodine or chlorine, or sulfonyloxy, for example methyl- or p-toluenesulfonyloxy, and $R_3$ is as defined for formula I.

Compounds of formula I wherein X is SO (sulfinyl) or $SO_2$ (sulfonyl) are prepared preferably by controlled oxidation of the corresponding compounds of formula I wherein X=S, for example using equimolar amounts or an excess of organic peracids, such as meta-chloroperbenzoic acid, or peroxides, for example tert-butyl hydroperoxide or cumene hydroperoxide.

Carboxylic acids of formula I, that is to say compounds of formula I wherein Y=OH, can be converted in a manner known per se into the corresponding carboxylic acid derivatives of formula I wherein Y is lower alkoxy, amino, lower alkylamino or di-lower alkylamino. Conversely, the mentioned carboxylic acid derivatives can be converted in a manner known per se into the free carboxylic acids of formula I, for example by reaction with LiOH/tetrahydrofuran/water/methanol, for example at a temperature of 50°. Furthermore, for example, compounds of formula I wherein Y is lower alkoxy can also be converted into the corresponding carboxylic acid derivatives of formula I wherein Y is amino, lower alkylamino or dialkylamino, for example by reaction with ammonia, alkylamines or dialkylamines.

If any intermediates comprise interfering reactive groups, for example carboxy, hydroxy, mercapto or amino groups, those groups can be temporarily protected by readily removable protecting groups. The choice of suitable protecting groups and the manner in which they are introduced and removed are known per se and are described, for example, in J. F. W. McOmie, Protective Groups in Organic Chemistry, Plenum Press, London, New York 1973.

Salts of compounds I can be prepared in a manner known per se. For example, acid addition salts of compounds I are obtained by treatment with a suitable acid or a suitable ion exchange reagent, and salts with bases are obtained by treatment with a suitable base or a suitable ion exchange reagent. Salts of compounds of formula I can be converted in customary manner into the free compounds I: acid addition salts, for example, by treatment with a suitable basic agent or a suitable ion exchange reagent, and salts with bases, for example, by treatment with a suitable acid or a suitable ion exchange reagent.

Salts of compounds I can be converted into different salts of compounds I in a manner known per se; acid addition salts can be converted, for example, into different acid addition salts, for example, by treating a salt of an inorganic acid, such as a hydrochloride, with a suitable metal salt, such as a sodium, barium or silver salt, of an acid, for example, with silver acetate, in a suitable solvent in which an inorganic salt being formed, for example silver chloride, is insoluble and is therefore excluded from the reaction mixture.

Depending on the procedure and reaction conditions, the compounds I having salt-forming properties can be obtained in free form or in the form of salts.

In view of the close relationship between the compounds I in free form and in the form of their salts, hereinbefore and hereinafter any reference to the free compounds I or their salts is to be understood as including also the corresponding salts or the free compounds I, respectively, where appropriate and expedient.

The compounds I, including the salts of salt-forming compounds, can also be obtained in the form of their hydrates and/or may comprise other solvents, for example solvents which may be used for the crystallisation of compounds present in solid form.

Depending on the starting materials and procedures chosen, the compounds I and their salts may be in the form of one of the possible isomers or in the form of a mixture of the same. Pure isomers obtainable may be, for example, pure diastereoisomers. Accordingly, mixtures of isomers may be, for example, mixtures of diastereoisomers. Mixtures of isomers of compounds I in free form or in salt form obtainable according to the process or by other methods can be separated in customary manner into their components; for example, they can be separated on the basis of the physicochemical differences between the constituents in known manner by fractional crystallisation, distillation and/or chromatography. The more active isomer is advantageously isolated.

The invention relates also to those forms of the process according to which a compound obtainable as intermediate at any stage of the process is used as starting material and the remaining steps are carried out or a starting material is used in the form of a derivative or salt or, especially, is formed under the reaction conditions.

In the process of the present invention it is preferable to use those starting materials and intermediates, in each case in free form or in salt form, which result in the compounds I or the salts thereof described in the introduction as being especially valuable. The invention relates also to novel starting materials and intermediates, in each case in tree form or in salt form, for the preparation of the compounds I or the salts thereof, to the use thereof and to processes for the preparation thereof, the variable R being as defined for the compounds I.

The invention relates also to the use of the compounds I and their pharmaceutically acceptable salts in the treatment or allergic conditions and disorders, preferably in the form of pharmaceutically acceptable compositions, especially in a method for the therapeutic treatment of the animal or human body, and to such a method of treatment.

The invention relates also to pharmaceutical compositions that comprise a compound I or a pharmaceutically acceptable salt thereof as active ingredient, and to processes for the preparation thereof. Those pharmaceutical compositions are compositions for enteral, such as oral and also rectal, administration, for parenteral administration, local administration and especially administration by inhalation to warm-blooded animals, especially humans, in which the pharmacological active ingredient is present alone or together with customary pharmaceutical excipients. The pharmaceutical compositions comprise (in percentages by weight), for example, approximately from 0.001% to 100%, preferably from approximately 0.1% to approximately 50%, active ingredient.

Pharmaceutical compositions for enteral or parenteral administration are, for example, compositions in unit dose forms, such as dragées, tablets, capsules or suppositories, and also ampoules. These are prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture or granules, if desired or necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, also carboxymethyl starch, crosslinked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are dry-filled capsules made of gelatin, and soft, sealed capsules made of gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and, where appropriate, stabilisers. In soft capsules, the active ingredient is preferably dissolved or suspended in suitable liquids, such as fatty oils, paraffin oil or liquid polyethylene glycols, to which stabilisers may also be added.

Suitable as rectally administrable pharmaceutical compositions are, for example, suppositories that comprise a combination of the active ingredient and a suppository base. Suitable suppository bases are, for example, natural or synthetic triglycerides, paraffin hydrocarbons, polyethylene glycols or higher alkanols. It is also possible to use gelatin rectal capsules that comprise a combination of the active ingredient and a base. Suitable bases are, for example, liquid triglycerides, polyethylene glycols or paraffin hydrocarbons.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions comprising viscosity-increasing substances, for example sodium carboxymethylcellulose, sorbitol and/or dextran, and, where appropriate, also stabilisers.

Pharmaceutical compositions for local administration are, for example for the topical treatment of the skin, lotions, creams and ointments, that is to say liquid or semi-solid oil-in-water or water-in-oil emulsions, fatty ointment,; that are non-aqueous, pastes, that is to say creams and ointments having secretion-absorbing pulverulent constituents, gels that are aqueous, have a low water content or are free of water and comprise swellable, gel-forming materials, foams, that is to say liquid oil-in-water emulsions in aerosol form that are administered from pressurised containers, and tinctures having an aqueous-ethanolic base, each of which may also comprise further customary pharmaceutical excipients, such as preservatives. Suitable for the local treatment of the eyes are, for example, eye drops that comprise the active ingredient in sterile aqueous or oily solution, and eye ointments that are preferably likewise prepared in sterile form. Suitable for the local treatment of the nose are, for example, sprays similar to those described hereinafter for the treatment of the respiratory tract, coarse powders that are administered by rapid inhalation through the nostrils, and especially nose drops that comprise the active ingredient in aqueous or oily solution. Suitable for the local treatment of the buccal cavity are, for example, lozenges and pastilles that comprise the active ingredient in an inert mass that is formed, for example, from sugar and gum arabic or gum tragacanth and to which flavourings may have been added. The preparation of the pharmaceutical compositions for local administration is effected in a manner known per se by mixing the active ingredient with the pharmaceutical excipients, for example by dissolving or suspending the active ingredient in the base or in part thereof, if necessary. For the preparation of emulsions in which the active ingredient is dissolved in one of the liquid phases, the active ingredient is generally dissolved in that phase prior to emulsification; for the preparation of suspensions in which the active ingredient is suspended in the emulsion, the active ingredient is mixed with part of the base after emulsification and then added to the rest of the formulation.

Pharmaceutical compositions for administration by inhalation are compositions in which the active ingredient is present in micronised form, that is to say in which the particle size of the active ingredient is less than 2 μm, especially less than 10 μm and advantageously less than 5 μm, for example micronised powders and aerosols that are administered in the form of sprays. The micronised powders comprise the active ingredient alone or together with an inert carrier, such as lactose, advantageously together with one of the propellants mentioned hereinafter. Aerosols are solutions, suspensions or emulsions of the active ingredient in a suitable, pharmaceutically acceptable liquid phase, such as in ethanol or water or in a corresponding mixture; they may, as required, also comprise other pharmaceutical excipients, such as non-ionic or anionic surface-active agents, emulsifiers and stabilisers, and/or other kinds of active ingredient, and they comprise a propellant, for example an inert gas, such as butane, under elevated pressure, or especially a readily volatile liquid that boils preferably under normal pressure below customary room temperature (for example at from approximately −30° C. to approximately +10° C.), such as an at least partially fluorinated polyhalogenated lower alkane, or a mixture of such liquids. In order to prepare the pharmaceutical compositions in a form ready for administration by inhalation, a corresponding pharmaceutical composition is introduced together with the propellant into suitable containers, such as vials or pressurised bottles provided with a suitable spray device, for example a valve. The valve is preferably designed in the form of a metering valve which, when operated, dispenses a predetermined amount of the container contents corresponding to a predetermined dose of the active ingredient. The procedure for preparing the finished pharmaceutical dosage form may also be such that suitable amounts of the pharmaceutical composition and of the propellant are introduced separately into the containers and only then are they mixed together.

The dose of the active ingredient may depend on various factors, such as the efficacy and the duration of efficacy of the active ingredient, the severity of the disorder to be treated or of its symptoms, the mode of administration, the species, sex, age and weight of the warm-blooded animal and/or the individual condition of the warm-blooded animal. In a normal case, the estimated daily dose, for example in the case of oral administration, for a warm-blooded animal weighing approximately 75 kg is from approximately 1 mg to approximately 150 mg, especially from approximately 2.5 to approximately 50 mg. That dose may be administered, for example, as a single dose or in several partial doses, for example of from 10 to 50 mg.

The following Examples illustrate the invention described above. Temperatures are given in degrees Celsius. DMF stands for dimethylformamide, ethyl acetate for acetic acid ethyl ester; hexane denotes an isomeric mixture of various hexanes (manufactured by Fluka).

Example 1: 4-[3-(2-quinolinylmethoxy)phenylamino]-2,2-diethyl-4-oxobutanoic acid A mixture of 0.87 g of 2,2-diethylsuccinic acid (H. Le Moal et al., Bull. Soc. Chim. 1964, 579–584) and 0.32 ml of acetyl chloride in 10 ml of dimethoxyethane is stirred for 2 hours at 85° and concentrated by evaporation using a rotary evaporator. The residue is treated twice with 30 ml of toluene each time and concentrated by evaporation again. The resulting anhydride is taken up in 25 ml of dimethoxyethane; 0.89 g of 3-(2-quinolinylmethoxy)aniline [J. H. Musser et al., J. Med. Chem. 32 (1989) 1176–1183] and 1.44 g of sodium acetate are added and the batch is stirred for 2 hours at 85° and concentrated by evaporation. The residue is suspended in 80 ml of 2N aqueous hydrochloric acid and the suspension is filtered. The precipitate is washed with water and crystallised from methanol to give the title compound in the form of colourless crystals of m.p. 149°–149.5°.

IR (methylene chloride): 3320, 3060, 2970, 2940, 2880, 2520, 1960, 1680, 1610, 1550, 1520, 1490, 1445, 1435, 1380, 1300, 1210, 1160, 1070, 970, 870, 830, 780, 750, 720, 690 cm$^{-1}$.

Example 2: 4-[3-(7-chloro-2-quinolinylmethoxy)phenylamino]-2,2-diethyl-4-oxobutanoic acid A mixture of 0.44 g of 2,2-diethylsuccinic acid and 1.6 ml of acetyl chloride in 10 ml of dimethoxyethane is stirred for 2 hours at 85° and concentrated by evaporation using a rotary evaporator. The residue is treated twice with 30 ml of toluene each time and concentrated by evaporation again. The resulting anhydride is taken up in 20 ml of dimethoxyethane; 0.51 g of 3-(7-chloro-2-quinolinylmethoxy)aniline and 0.75 g of sodium acetate are added and the batch is stirred for 5 days at 20° and concentrated by evaporation. The residue is suspended in 80 ml of 2N aqueous hydrochloric acid and the suspension is filtered. The precipitate is washed with water and crystallised from methanol to give the title compound in the form of colourless crystals of m.p. 151°–153°. IR (KBr): 3300, 2970, 2880, 1680, 1620, 1600, 1550, 1500, 1440, 1420, 1290, 1200, 1160, 1080, 940, 870, 850, 780, 680 cm$^{-1}$. TLC (hexane/ethyl acetate 1:1): $R_f$=0.17.

The starting material is prepared as follows:

(a) 3-(7-chloro-2-quinolinylmethoxy)aniline: 1.8 ml of a 5.4M methanolic sodium methoxide solution are added to a solution of 1.02 g of 3-aminophenol in 25 ml of abs. methanol and the batch is stirred for 10 min. at 20° and concentrated by evaporation. The residue is taken up in 20 ml of abs. DMF, and a solution of 2.97 g of 2-bromomethyl-7-chloroquinoline [R. Zamboni, J. Med. Chem. 35 (1992) 3832–3844] in 10 ml of abs. DMF is added dropwise at 10°. The reaction mixture is stirred for 2 hours at 10° and for 12 hours at 20° and then concentrated by evaporation. The residue is taken up in methylene chloride, washed with water, dried over sodium sulfate and concentrated to dryness using a rotary evaporator. Chromatographic purification of the residue on 200 g of silica gel using hexane/ethyl acetate 3:2 gives the title compound in the form of an orange oil which crystallises; m.p. 87.5°–88.5°.

Example 3: 4-[3-(7-fluoro-2-quinolinylmethoxy)phenylamino]-2,2-diethyl-4-oxobutanoic acid A mixture of 2.14 g of 2,2-diethylsuccinic acid and 1.6 ml of oxalyl chloride in 90 ml of methylene chloride is stirred for 5 hours at 30° and concentrated by evaporation using a rotary evaporator. The residue is taken up in 10 ml of methylene chloride and poured into a solution of 1.65 g of 3-(7-fluoro-2-quinolinylmethoxy)aniline in 45 ml of methylene chloride and 45 ml of pyridine. The reaction mixture is stirred for 16 hours at 20° and concentrated by evaporation. The residue is suspended in 150 ml of 2N aqueous hydrochloric acid and the suspension is filtered. The precipitate is washed with water and crystallised from methanol to give the title compound in the form of colourless crystals of m.p. 164°–165° (which turn a reddish colour on melting). IR (KBr): 3319, 2968, 1687, 1599, 1546, 1514, 1492, 1436, 1375, 1290, 1207, 1174, 1114, 1066, 965,846, 774 cm⁻¹. TLC (methylene chloride/methanol 19:1): $R_f$=0.25.

The starting materials are prepared as follows:

(a) 2-bromomethyl-7-fluoroquinoline: 21.58 g of N-bromosuccinimide and 0.21 g of azoisobutyronitrile are added to a solution of 13.03 g of 2-methyl-7-fluoroquinoline [Z. Song et al., J. Heterocyclic Chem. 30 (1993) 17–21] in 150 ml of carbon tetrachloride. The resulting suspension is boiled under reflux for 27 hours, filtered and concentrated by evaporation. The residue is chromatographed on silica gel using hexane/ethyl acetate 9:1 to 7:3. The title compound is obtained in the form of colourless crystals of m.p. 101°–102°.

(b) 3-(7-fluoro-2-quinolinylmethoxy)aniline: 1.99 g of sodium carbonate are added to a solution of 1.36 g of 3-aminophenol in 150 ml of acetone and the batch is stirred for 15 min. at 20°. 3.0 g of 2-bromomethyl-7-fluoroquinoline, 4.07 g of caesium carbonate and 0.1 g of potassium iodide are added to the mixture which is boiled under reflux for 3 hours. The reaction mixture is filtered, the precipitate is washed with acetone and the filtrate is concentrated by evaporation. The residue is taken up in methylene chloride, washed with water, dried over sodium sulfate and concentrated by evaporation. The resulting orange oil is chromatographed on 200 g of silica gel using hexane/ethyl acetate 3:1. The title compound is obtained in the form of a yellow solid of m.p. 88°–89°.

Example 4: 4-[3-(7-trifluoromethyl-2-quinolinylmethoxy)phenylamino]-2,2-diethyl-4-oxobutanoic acid A mixture of 0.52 g of 2,2-diethylsuccinic acid and 1.9 ml of acetyl chloride in 10 ml of dimethoxyethane is stirred for 1.5 hours at 85° and concentrated by evaporation using a rotary evaporator. The residue is taken up in 20 ml of dimethoxyethane; 0.64 g of 3-(7-trifluoromethyl-2-quinolinylmethoxy)aniline and 1.21 g of sodium acetate are added and the batch is stirred for 3 hours at 20° and concentrated by evaporation. The residue is suspended in 80 ml of 2N aqueous hydrochloric acid and the suspension is filtered. The precipitate is washed with water and crystallised from methanol to give the title compound in the form of colourless crystals of m.p. 173°–175°. IR (KBr): 3318, 2971, 1709, 1667, 1600, 1536, 1495, 1429, 1321, 1299, 1262, 1188, 1127, 1056, 895, 862, 773, 683 cm⁻¹. TLC (hexane/ethyl acetate 1:1): $R_f$=0.30.

The starting materials are prepared as follows:

(a) 2-bromomethyl-7-trifluoromethylquinoline: 18.26 g of N-bromosuccinimide and 0.2 g of azoisobutyronitrile are added to a solution of 14.45 g of 2-methyl-7-trifluoromethylquinoline [U.S. Pat. No. 2,432,393 (Eastman Kodak Co., 1943)] in 150 ml of carbon tetrachloride. The resulting suspension is boiled under reflux for 72 hours, filtered and concentrated by evaporation. The residue is chromatographed on silica gel using hexane/ethyl acetate 3:2. The title compound is obtained in the form of a yellow solid of m.p. 71°–72°.

(b) 3-(7-trifluoromethyl-2-quinolinylmethoxy)aniline: 3.0 g of sodium carbonate are added to a solution of 2.0 g of 3-aminophenol in 200 ml of acetone and the mixture is stirred for 15 min. at 50°. 5.2 g of 2-bromomethyl-7-trifluoromethylquinoline, 6.1 g of caesium carbonate and 0.1 g of potassium iodide are added thereto and boiling under reflux is carried out for 2 hours. The reaction mixture is filtered, the precipitate is washed with acetone and the filtrate is concentrated by evaporation. The residue is taken up in hexane/ethyl acetate 3:2 and filtered over silica gel. The filtrate is concentrated by evaporation and the resulting oil is chromatographed on 400 g of silica gel using hexane/ethyl acetate 3:2. The title compound is obtained in the form of a yellow solid of m.p. 85°–86°.

Example 5: 4-[7-(2-quinolinylmethoxy)naphth-2-ylamino]-2,2-diethyl-4-oxobutanoic acid A mixture of 1.16 g of 2,2-diethylsuccinic acid and 4.1 ml of acetyl chloride is stirred for 2 hours at 52° and concentrated by evaporation using a rotary evaporator. The residue is treated twice with 50 ml of toluene each time and concentrated by evaporation again. The resulting anhydride is taken up in 20 ml of dimethoxyethane; 1.0 g of 7-(2-quinolinylmethoxy)napth-2-ylamine [U.S. Pat. No. 4,719, 308 (American Home Products, 1986)] and 1.37 g of sodium acetate are added and the batch is stirred for 2 hours at 85° and concentrated by evaporation. The residue is suspended in 80 ml of 2N aqueous hydrochloric acid and the suspension is filtered. The precipitate is washed with water and crystallised from methanol to give the title compound in the form of colourless crystals of m.p. 190°–191°.

Example 6: 4-[7-(7-fluoro-2-quinolinylmethoxy)naphth-2-ylamino]-2,2-diethyl-4-oxobutanoic acid A mixture of 0.67 g of 2,2-diethylsuccinic acid and 1.85 ml of acetyl chloride is stirred for 2 hours at 52° and concentrated by evaporation using a rotary evaporator. The residue is treated twice with 20 ml of toluene each time and concentrated by evaporation again. The anhydride is taken up in 10 ml of dimethoxyethane; 0.47 g of 7-(7-fluoro-2-quinolinylmethoxy)napth-2-ylamine and 0.61 g of sodium acetate are added and the batch is stirred for 2 hours at 85° and concentrated by evaporation. The residue is suspended in 40 ml of 2N aqueous hydrochloric acid and the suspension is filtered. The precipitate is washed with water and crystallised from methanol to give the title compound in the form of colourless crystals of m.p. 196°–198°.

The starting material is prepared as follows:

(a) 7-(7-fluoro-2-quinolinylmethoxy)naphth-2-ylamine: 0.86 g of 2-amino-7-hydroxynaphthalene is added to a solution of 0.13 g of sodium in 10 ml of methanol and the batch is stirred for 1 hour at room temperature. The methanol is evaporated off in vacuo and the residue is dissolved in 13 ml of DMF. A solution of 1.3 g of 2-bromomethyl-7-fluoroquinoline (Example 3a) in 5 ml of DMF is added and the batch is stirred for 6 hours at room temperature. After the addition of 100 ml of water, the precipitate obtained is isolated by filtration and crystallised from ethyl acetate to give the title compound in the form of pale yellow crystals of m.p. 164.5°–165.5°.

Example 7: 4-[3-(7-fluoro-2-quinolinylmethylthio)phenylamino]-2,2-diethyl-4-oxobutanoic acid A mixture of 0.95 g of 2,2-diethylsuccinic acid and 2.6 ml of acetyl chloride is stirred for 2 hours at 52° and concentrated by evaporation using a rotary evaporator. The residue is treated twice with 30 ml of toluene each time and concentrated by evaporation again. The resulting anhydride is taken up in 10 ml of dimethoxyethane; 0.6 g of 3-(7-fluoro-2-quinolinylmethylthio)phenylamine [=3-(7-fluoro-2-quinolinylmethylthio)aniline] and 0.86 g of sodium acetate are added and the batch is stirred for 2 hours at 85° and concentrated by evaporation. The residue is chromatographed on silica gel using methylene chloride/methanol 95:5. First some fractions are obtained that contain small amounts of impurities; the reactions containing the product are then eluted. The eluant is evaporated off under reduced pressure and the residue is crystallised from ethyl acetate to give the title compound in the form of beige crystals of m.p. 132°–134°.

The starting material is obtained as follows:

(a) 3-(7-fluoro-2-quinolinylmethylthio)phenylamine: 0.86 g of 3-aminothiophenol is added to a solution of 0.13 g of sodium in 10 ml of methanol and the batch is stirred for 1 hour at room temperature. The methanol is evaporated off in vacuo and the residue is dissolved in 13 ml of DMF. A solution of 1.3 g of 2-bromomethyl-7-fluoroquinoline in 5 ml of DMF is added and the batch is stirred for 6 hours at room temperature. After the addition of 100 ml of water, extraction is carried out three times with 20 ml of ethyl acetate each time and the combined extract are dried over sodium sulfate. After filtration and concentration by evaporation using a rotary evaporator, the residue is crystallised from ether/n-pentane 1:1 to give the title compound in the form of pale yellow crystals of m.p. 70°–71°.

Example 8: 4-[3-(7-fluoro-2-quinolinylmethoxy)phenylamino]-2,2-diethyl-4-oxobutanoic acid methyl ester A solution of diazomethane in diethyl ether is added at 0° to a solution of 1.9 g of 4-[3-(7-fluoro-2-quinolinylmethoxy)phenylamino]-2,2-diethyl-4-oxobutanoic acid (Example 3) in 150 ml of tetrahydrofuran until a yellow colour remains established. The yellow solution is immediately concentrated by evaporation to give the title compound in the form of a colourless oil which crystallises on being left to stand in a refrigerator, m.p. 92°–93°; IR (methylene chloride): 1735 cm$^{-1}$ (C=O).

Example 9: The following compounds are prepared analogously to the compounds described in Examples 1–8:

(a) 4-[3-(6-fluoro-2-quinolinylmethoxy)phenylamino]-2,2-diethyl-4-oxobutanoic acid, m.p. 125°–130°, (b) 4-[3-(8-fluoro-2-quinolinylmethoxy)phenylamino]-2,2-diethyl-4-oxobutanoic acid, m.p. 150°–152°, (c) 4-[3-(6-chloro-2-quinolinylmethoxy)phenylamino]-2,2-diethyl-4-oxobutanoic acid, (d) 4-[3-(8-chloro-2-quinolinylmethoxy)phenylamino]-2,2-diethyl-4-oxobutanoic acid, (e) 4-[3-(7-methyl-2-quinolinylmethoxy)phenylamino]-2,2-diethyl-4-oxobutanoic acid, m.p. 162°–163°, (f) 4-[3-(6-methyl-2-quinolinylmethoxy)phenylamino]-2,2-diethyl-4-oxobutanoic acid, m.p. 175°.

(g) 4-[3-(8-methyl-2-quinolinylmethoxy)phenylamino]-2,2-diethyl-4-oxobutanoic acid, (h) 4-[3-(7-methoxy-2-quinolinylmethoxy)phenylamino]-2,2-diethyl-4-oxobutanoic acid, m.p. 163°–164°, (i) 4-[3-(6-methoxy-2-quinolinylmethoxy)phenylamino]-2,2-diethyl-4-oxobutanoic acid, (j) 4-[3-(8-methoxy-2-quinolinylmethoxy)phenylamino]-2,2-diethyl-4-oxobutanoic acid, (k) 4-[3-(7-bromo-2-quinolinylmethoxy)phenylamino]-2,2-diethyl-4-oxobutanoic acid, m.p. 175°, (l) 4-[3-(7-nitro-2-quinolinylmethoxy)phenylamino]-2,2-diethyl-4-oxobutanoic acid, (m) 4-[3-(7-cyano-2-quinolinylmethoxy)phenylamino]-2,2-diethyl-4-oxobutanoic acid, (n) 4-[3-(7-methylthio-2-quinolinylmethoxy)phenylamino]-2,2-diethyl-4-oxobutanoic acid, (o) 4-[3-(7-acetyl-2-quinolinylmethoxy)phenylamino]-2,2-diethyl-4-oxobutanoic acid, m.p. 164°, (p) 4-[3-(7-benzyloxy-2-quinolinylmethoxy)phenylamino]-2,2-diethyl-4-oxobutanoic acid, m.p. 89°–95°, (q) 4-[3-(7-(2-phenylethyloxy)-2-quinolinylmethoxy)phenylamino]-2,2-diethyl-4-oxobutanoic acid, (r) 4-[3-(7-(4-phenylbutyloxy)-2-quinolinylmethoxy)phenylamino]-2,2-diethyl-4-oxobutanoic acid, (s) 4-[3-(7-fluoro-2-quinolinylmethylthio)phenylamino]-2,2-diethyl-4-oxobutanoic acid, m.p. 132°–134°, (t) 4-[3-(7-chloro-2-quinolinylmethylthio)phenylamino]-2,2-diethyl-4-oxobutanoic acid, (u) 4-[3-(2-quinolinylmethylthio)phenylamino]-2,2-diethyl-4-oxobutanoic acid, (v) 4-[3-(7fluoro-2-quinolinylmethylsulfonyl)phenylamino]-2,2-diethyl-4-oxobutanoic acid (by oxidation of the compound of Example 7 with meta-chloroperbenzoic acid in excess), (w) 4-[3-(7-chloro-2-quinolinylmethylsulfonyl)phenylamino]-2,2-diethyl-4-oxobutanoic acid (by oxidation of the compound of Example 9t with meta-chloroperbenzoic acid in excess), (x) 4-[3-(2-quinolinylmethylsulfonyl)phenylamino]-2,2-diethyl-4-oxobutanoic acid (by oxidation of the compound of Example 9u with meta-chloroperbenzoic acid in excess), (y) 4-[7-(7-fluoro-2-quinolinylmethoxy)naphth-2-ylamino]-2,2-diethyl-4-oxobutanoic acid, m.p. 196°–198°, (z) 4-[7-(7-chloro-2-quinolinylmethoxy)naphth-2-ylamino]-2,2-diethyl-4-oxobutanoic acid, (aa) 4-[7-(2-quinolinylmethoxy)naphth-2-ylamino]-2,2-diethyl-4-oxobutanoic acid, m.p. 190°–191°, (ab) 4-[N-(4-carboxybenzyl)-3-(7-fluoro-2-quinolinylmethoxy)phenylamino]-2,2-diethyl-4-oxobutanoic acid methyl ester [1.N-alkylation of 3-(7-fluoro-2-quinolinylmethoxy)aniline, Example 3b, with 4-carboxybenzyl bromide; 2. Reaction of the resulting N-(4-carboxybenzyl)-3-(7-fluoro-2-quinolinylmethoxy)aniline with 3-ethyl-3-methoxycarbonyl-pentanoic acid (=methyl semiester of 2,2-diethylsuccinic acid)], (ac) 4-[N-(3-carboxybenzyl)-3-(7-fluoro-2-quinolinylmethoxy)phenylamino]-2,2-diethyl-4-oxobutanoic acid methyl ester (from N-(3-carboxybenzyl)-3-(7-fluoro-2-quinolinylmethoxy)aniline, analogously to Example 9ab), (ad) 4-[N-(2-carboxybenzyl)-3-(7-fluoro-2-quinolinylmethoxy)phenylamino]-2,2-diethyl-4-oxobutanoic acid methyl ester (frown N-(2-carboxybenzyl)-3-(7-fluoro-2-quinolinylmethoxy)aniline, analogously to Example 9ab), (ae) 4-[N-(3-carboxypropyl)-3-(7-fluoro-2-quinolinylmethoxy)phenylamino]-2,2-diethyl-4-oxobutanoic acid (analogously to Example 3 from N-(3-carboxypropyl)-3-(7-fluoro- 2-quinolinylmethoxy)aniline instead of 3-(7-fluoro-2-quinolinylmethoxy)aniline), (af) 4-[N-methyl-3-(7-fluoro-2-quinolinylmethoxy)phenylamino]-2,2-diethyl-4-oxobutanoic acid methyl ester (from 4-[3-(7-fluoro-2-quinolinylmethoxy)phenylamino]-2,2-diethyl-4-oxobutanoic acid, Example 3, by reaction with 2 equivalents of NaH and then 2 equivalents of methyl iodide), (ag) 4-[N-methyl-3-(7-fluoro-2-quinolinylmethoxy)phenylamino]-2,2-diethyl-4-oxobutanoic acid (from 4-[N-methyl-3-(7-fluoro-2-quinolinylmethoxy)phenylamino]-2,2-diethyl-4-oxobutanoic acid methyl ester, Example 9af, (1) by hydrolysis with LiOH/methanol/tetrahydrofuran/water or (2) by reaction with 3 equivalents of trimethylchlorosilane/sodium iodide in acetonitrile at 60°), (ah) 4-[3-(7-fluoro-2-quinolinylmethoxy)phenylamino]-2,2-dimethyl-4-oxobutanoic acid (analogously to Example 3 from 2,2-dimethylsuccinic acid instead of 2,2-diethylsuccinic acid), m.p. 209°–210°, (ai) 4-[3-(7-fluoro-2-quinolinylmethoxy)phenylamino]-2-ethyl-2-methyl-4-oxobutanoic acid (analogously to Example 3 from 2-ethyl-2-methylsuccinic acid instead of 2,2-diethylsuccinic acid), m.p. 179°–180°, (aj) 1-[3-(7-fluoro-2-quinolinylmethoxy)phenylaminocarbonylmethyl]-cyclopentanecarboxylic acid [analogously to Example 3 from 2-(1-carboxycyclopentyl)-acetic acid (Bull. Soc. Chim. Fr. 1964, 579–584) instead of 2,2-diethylsuccinic acid], m.p. 187°–188°, (ak) 1-[3-(7-fluoro-2-quinolinylmethoxy)phenylaminocarbonylmethyl]-cyclohexanecarboxylic acid [analogously to Example 3 from 2-(1-carboxycyclohexyl)-acetic acid (Bull. Soc. Chim. Fr. 1964, 579–584) instead of 2,2-diethylsuccinic acid], m.p. 190°–191°, (al) 4-[3-(7-chloro-2-quinolinylmethoxy)phenylamino]-2,2-dimethyl-4-oxobutanoic acid (analogously to Example 2 from 2,2-dimethylsuccinic acid instead of 2,2-diethylsuccinic acid), (am) 4-[3-(2-quinolinylmethoxy)phenylamino]-2-ethyl-2-methyl-4-oxobutanoic acid (analogously to Example 1 from 2-ethyl-2-methylsuccinic acid instead of 2,2-diethylsuccinic acid), (an) 4-[3-(2-quinolinylmethoxy)phenylamino]-2,2-di-n-propyl-4-oxobutanoic acid (analogously to Example 1 from 2,2-di-n-propylsuccinic acid instead of 2,2-diethylsuccinic acid), (ao) 4-[3-(2-quinolinylmethoxy)phenylamino]-2,2-diethyl-4-oxobutanoic acid methyl ester (from the compound of Example 1 by esterification with, for example, diazomethane), (ap) 4-[3-(7-chloro-2-quinolinylmethoxy)phenylamino]-2,2-diethyl-4-oxobutanoic acid methyl ester (from the compound of Example 2 by esterification with, for example, diazomethane), (aq) 4-[3-(7-chloro-2-quinolinylmethoxy)phenylamino]-2,2-diethyl-4-oxobutanoic acid amide (from 4-[3-(7-chloro-2-quinolinylmethoxy)phenylamino]-2,2-diethyl-4-oxobutanoic acid methyl ester, Example 9ap, by reaction with, for example, $NH_3$), (ar) 4-[3-(7-chloro-2-quinolinylmethylsulfinyl)phenylamino]-2,2-diethyl-4-oxobutanoic acid (by oxidation of 4-[3-(7-chloro-2-quinolinylmethylthio)phenylamino]-2,2-diethyl-4-oxobutanoic acid, Example 9t, with, for example, meta-chloroperbenzoic acid), (as) 4-[3-(6,7-dimethyl-2-quinolinylmethoxy)phenylamino]-2,2-diethyl-4-oxobutanoic acid [starting from 2,6,7-trimethylquinoline (Tetrahedron 39, 1983, 2831–2841) analogously to Example 3], m.p. 184°.

Example 10: 4-[3-(6-fluoro-2-quinolinylmethoxy)phenylamino]-2,2-diethyl-4-oxobutanoic acid A mixture of 0.34 g of 2,2-diethylsuccinic acid and 0.2 ml of acetyl chloride is stirred for 2 hours at 52° and concentrated by evaporation using a rotary evaporator. The residue is treated twice with 20 ml of toluene each time and concentrated by evaporation again. The resulting 2,2-diethylsuccinic acid anhydride is dissolved in 3 ml of dichloromethane; 0.2 g of 3-(6-fluoro-2-quinolinylmethoxy)aniline and 3 ml of pyridine are added and the batch is stirred for 4 hours at room temperature and hydrolysed with 100 ml of water. The organic phase is separated off in a separating funnel and the aqueous phase is extracted twice with 10 ml of dichloromethane each time. After drying over sodium sulfate and evaporating the solvent in vacuo, the residue is recrystallised from methanol to give the title compound in the form of colourless crystals of m.p. 125°–130°.

The starting material is prepared as follows:

(a) 2-bromomethyl-6-fluoroquinoline: 11.5 g of N-bromosuccinimide and 0.1 g of azobisisobutyronitrile are added to a solution of 7.0 g of 2-methyl-6-fluoroquinoline [Song et al., J. Heterocyclic Chem. 30 (1993) 17–21] in 60 ml of tetrachloromethane, and the batch is heated under reflux for 7 hours, filtered and concentrated by evaporation. The residue is chromatographed on silica gel using hexane/ethyl acetate 3:2. The title compound is obtained in the form of yellow crystals of m.p. 88°–90°.

(b) 3-(6-fluoro-2-quinolinylmethoxy)aniline: 1.74 g of 3-aminophenol are added to a solution of 0.3 g of sodium in 15 ml of methanol and the batch is stirred for 1 hour at room temperature. The methanol is evaporated off in vacuo and the residue is dissolved in 30 ml of dimethylformamide. A solution of 3.0 g of 2-bromomethyl-6-fluoroquinoline in 12 ml of dimethylformamide is added and the batch is stirred for 12 hours at room temperature. The solvent is evaporated off in vacuo and 100 ml of water are added to the residue. The batch is extracted with ethyl acetate (twice, 15 ml each time) and dried over sodium sulfate. After filtration and evaporation of the solvent in vacuo, the residue is chromatographed on silica gel using hexane/ethyl acetate 1:1 to give the title compound in the form of a pale yellow oil. $^1$H-NMR (300 MHz, $CDCl_3$): delta=5.33 (s, 2H: $CH_2$), 6.20–6.39 (m, 2H), 6.43 (m, 1H), 7.04 (m, 1H), 7.42–7.56 (m, 2H), 7.69 (d, 1H), 8.07 (m, 1H), 8.14 (d, 1 H) ppm.

Example 11: 4-[7-(6-fluoro-2-quinolinylmethoxy)naphth-2-ylamino]-2,2-diethyl-4-oxobutanoic acid Analogously to Example 6, the title compound is obtained in the form of beige crystals of m.p. 191°–196° starting from 1.3 g of 2,2-diethylsuccinic acid and 0.92 g of 7-(6-fluoro-2-quinolinylmethoxy)naphth-2-ylamine.

The starting material is prepared as follows:

(a) 7-(6-fluoro-2-quinolinylmethoxy)naphth-2-ylamine: Analogously to Example 6(a), the title compound is obtained starting from 5.3 g of 2-amino-7-hydroxynaphthalene and 8.0 g of 2-bromomethyl-6-fluoroquinoline (Example 10a); $^1$H-NMR (300 MHz, $CDCl_3$): delta=5.45 (s, 2H: $CH_2$), 6.80 (dd, 1H), 6.85 (d, 1H), 7.10 (d, 1H), 7.40 (dd, 1H), 7.45 (dd, 1H), 7.52 (dt, 1H), 7.58 (d, 1H), 7.63 (d, 1H), 7.73 (d, 1H), 8.10 (dd, 1H), 8.14 (d, 1H) ppm.

Example 12: 4-[3-(6-fluoro-2-quinolinylmethylthio)phenylamino]-2,2-diethyl-4-oxobutanoic acid Analogously to Example 7, the title compound is obtained in the form of beige crystals of m.p. 117°–120° starting from 4.48 g of 2,2-diethylsuccinic acid and 2.40 g of 3-(6-fluoro-2-quinolinylmethylthio)aniline.

The starting material is prepared as follows:

(a) 3-(6-fluoro-2-quinolinylmethylthio)aniline: Analogously to Example 7(a), the title compound is obtained in the form of crystals of m.p. 69°–73° starting from 3.49 g of 3-aminothiophenol and 6.70 g of 2-bromomethyl-6-fluoroquinoline [Example 10(a)].

Example 13: 4-[3-(8-fluoro-2-quinolinylmethoxy)phenylamino]-2,2-diethyl-4-oxobutanoic acid Analogously to Example 10, the title compound is obtained in the form of beige crystals of m.p. 150°–152° starting from 4.68 g of 2,2-diethylsuccinic acid and 2.80 g of 3-(8-fluoro-2-quinolinylmethoxy)aniline.

The starting material is prepared as follows:

(a) 2-methyl-8-fluoroquinoline: 45.6 g of 2-fluoroaniline are placed in 450 ml of 2-butanol, and 140 ml of a 6.6 molar solution of HCl in 2-butanol and 155.6 g of chloranil are added. The mixture is heated to reflux temperature, with stirring. A solution of 40.0 g of crotonaldehyde in 120 ml of 2-butanol is then added dropwise to the reaction mixture and the batch is heated under reflux for 50 min. After cooling, the solvent is largely evaporated off in vacuo, 700 ml of tetrahydrofuran are added and the batch is heated under reflux for 30 min. After cooling, the precipitate is isolated by filtration and partitioned between 1 liter of 2N aqueous sodium hydroxide solution and 400 ml of dichloromethane. The organic phase is separated off and the aqueous phase is extracted twice more with 200 ml of dichloromethane each time. Drying over sodium sulfate, filtration and evaporation of the solvent in vacuo and chromatography of the residue on silica gel using dichloromethane give the title compound; $^1$H-NMR (300 MHz, $CDCl_3$): delta=2.80 (s, 3H, $CH_3$), 7.31–7.44 (m, 3H), 7.55 (m, 1H), 8.05 (dd, 1H) ppm.

(b) 2-bromomethyl-8-fluoroquinoline: Analogously to Example 10(a), the title compound is obtained in the form of pale yellow crystals of m.p. 89°–93° starting from 10 g of 2-methyl-8-fluoroquinoline and 16.5 g of N-bromosuccinimide.

(c) 3-(8-fluoro-2-quinolinylmethoxy)nitrobenzene: 0.67 g of 3-nitrophenol and 1.15 g of 2-bromomethyl-8-fluoroquinoline are dissolved in 110 ml of ethyl methyl ketone; 3.3 g of potassium carbonate and 0.8 g of potassium iodide are added and the batch is heated under reflux for 3 hours. After cooling, removing the solid by filtration and evaporating the solvent in vacuo, 100 ml of dichloromethane are added to the residue, the batch is washed with water (twice, 20 ml each time), dried over sodium sulfate, filtered and freed of the solvent in vacuo to give the title compound in the form of pale yellow crystals of m.p. 128°–129° after recrystallisation from dichloromethane/hexane.

(d) 3-(8-fluoro-2-quinolinylmethoxy)aniline: 1.2 g of 3-(8-fluoro-2-quinolinylmethoxy)nitrobenzene are dissolved in 40 ml of tetrahydrofuran; 3.5 g of Raney nickel are added and the batch is hydrogenated at room temperature and under normal pressure. After filtering off the catalyst and evaporating the solvent in vacuo, the residue is chromatographed on silica gel using dichloromethane/hexane/ethyl acetate 6:3:1. The title compound is obtained in the form of pale yellow crystals of m.p. 94°–97°.

Example 14: 4-[7-(8-fluoro-2-quinolinylmethoxy)naphth-2-ylamino]-2,2-diethyl-4-oxobutanoic acid Analogously to Example 6, the title compound is obtained in the form of beige crystals of m.p. 193°–196° starting from 0.41 g of 2,2-diethylsuccinic acid and 0.29 g of 7-(8-fluoro-2-quinolinylmethoxy)naphth-2-ylamine.

The starting material is prepared as follows:

(a) 7-(8-fluoro-2-quinolinylmethoxy)naphth-2-ylamine: Starting from 3.3 g of 2-amino-7-hydroxynaphthalene and 5.0 g of 2-bromomethyl-8-fluoroquinoline [Example 13(b)], the title compound is obtained in the form of beige crystals of m.p. 141°–142° analogously to Example 6(a).

Example 15: 4-[3-(8-fluoro-2-quinolinylmethylthio)phenylamino]-2,2-diethyl-4-oxobutanoic acid Analogously to Example 7, the title compound is obtained in the form of beige crystals of m.p. 113°–115° starting from 4.97 g of 2,2-diethylsuccinic acid and 3.15 g of 3-(8-fluoro-2-quinolinylmethylthio)aniline.

The starting material is prepared as follows:

(a) 3-(8-fluoro-2-quinolinylmethylthio)aniline: Starting from 2.72 g of 3-aminothiophenol and 5.20 g of 2-bromomethyl-8-fluoroquinoline [Example 13(b)], the title compound is obtained in the form of crystals of m.p. 80°–83° analogously to Example 7(a).

Example 16: 4-[3-(6,7-difluoro-2-quinolinylmethoxy)phenylamino]-2,2-diethyl-4-oxobutanoic acid Analogously to Example 3, the title compound is prepared from 2,2-diethylsuccinic acid and 3-(6,7-difluoro-2-quinolinylmethoxy)aniline. It is obtained in the form of a white solid; $^1$H-NMR, 200 MHz, DMSO, delta (ppm)=9.90 (s, 1H), 8.42 (d, 1H), 8.10 (m, 2H), 7.70 (d, 1H), 7.45 (m, 1H), 7.07 (m, 2H), 6.73 (d, 1H), 5.35 (s, 2H), 2.58 (s, 2H), 1.80 (m, 4H), 0.80 (t, 6H).

The starting materials are prepared as follows:

(a) 2-methyl-6,7-difluoroquinoline: Starting from 3,4-difluoroaniline, the title compound is prepared analogously to Example 13(a) by reaction with crotonaldehyde and chloranil in 2-butanol [see also J. Heterocycl. Chem. 30 (1993) 17–21].

(b) 3-(6,7-difluoro-2-quinolinylmethoxy)aniline: Starting from 2-methyl-6,7-difluoroquinoline, the title compound is prepared analogously to Example 3(a) [NBS-bromination] and Example 3(b) [reaction with 3-aminophenol]: $^1$H-NMR, 200 MHz, DMSO, delta (ppm)=8.42 (d, 1H), 8.10 (m, 2H), 7.67 (d, 1H), 7.45 (m, 1H), 6.90 (t, 1H), 6.20 (m, 3H), 5.25 (s, 2H), 5.08 (s, 2H).

Example 17: 4-[N-(4-carboxy-2-methoxybenzyl)-3-(7-fluoro-2-quinolinylmethoxy)phenyl]amino]-2,2-diethyl-4-oxobutanoic acid 0.12 g of 4-[N-(4-methoxycarbonyl-2-methoxybenzyl)-3-(7-fluoro-2-quinolinylmethoxy)phenyl]amino]-2,2-diethyl-4-oxobutanoic acid methyl ester (Example 17A) and 2 ml of 10N sodium hydroxide solution are boiled under reflux for 20 hours in water/methanol/tetrahydrofuran 1:1:1. The batch is then adjusted to a pH of approximately 2 by the addition of 1N HCl and extracted three times with methylene chloride/isopropanol 4:1. The combined organic phases are washed with saturated sodium chloride solution, dried (magnesium sulfate) and concentrated by evaporation. The residue is stirred in diethyl ether, filtered and dried to give the title compound in the form of a white amorphous solid; $^1$H-NMR, 400 MHz, DMSO, delta (ppm)=8.40 (d, 2H), 8.05 (dd, 1H), 7.67 (dd, 1H), 7.58 (d, 1H), 7.2–7.5 (m, 4H), 7.0 (m, 1H), 6.86 (m, 1H), 6.75 (m, 1H), 5.37 (s, 2H), 4.80 (s, 2H), 3.68 (s, 3H), 2.30 (s, 2H), 1.50 (q, 4H), 0.6 (t, 6H).

Example 17A: 4-[N-(4-methoxycarbonyl-2-methoxybenzyl)-3-(7-fluoro-2-quinolinylmethoxy)phenyl]amino]-2,2-diethyl-4-oxobutanoic acid methyl ester 0.1 g of 3-ethyl-3-methoxycarbonyl-pentanoic acid (=methyl semiester of 2,2-diethylsuccinic acid; see Bull. Soc. Chim. 1964, 828), 0.38 g of N-ethyl-N-(3-dimethylaminopropyl)-carbodiimide hydrochloride and 0.24 g of 4-dimethylamino-pyridine are added to a solution of 0.22 g of N-(4-methoxycarbonyl-2-methoxybenzyl)-3-(7-fluoro-2-quinolinylmethoxy)aniline in 20 ml of methylene chloride. The reaction mixture is stirred under argon for 72 hours at room temperature. 100 ml of ethyl acetate are then added to the reaction mixture, and the resulting turbid solution is washed three times with water and once with saturated sodium chloride solution, dried (magnesium sulfate) and concentrated by evaporation. The residue is purified on silica gel (hexane/ethyl acetate 3:2) to give the title compound in the form of an oil; $^1$H-NMR, 200 MHz, CDCl$_3$, delta (ppm)=8.17 (d, 1H), 7.83 (dd, 1H), 7.70 (dd, 1H), 7.55 (d, 2H), 7.40-7.18 (m, 4H), 6.95 (dd, 1H), 6.65 (m, 2H), 5.30 (s, 2H), 4.90 (s, 2H), 3.90 (s, 3H), 3.70 (2s, 6H), 2.37 (s, 2H), 1.60 (q, 4H), 0.65 (t, 6H).

The starting material is prepared as follows:

(a) N-(4-methoxycarbonyl-2-methoxybenzyl)-3-(7-fluoro-2-quinolinylmethoxy)aniline: A mixture consisting of 0.536 g of 3-(7-fluoro-2-quinolinylmethoxy)aniline, 0.518 g of 3-methoxy-4-bromomethyl-benzoic acid methyl ester, 1.0 g of sodium carbonate and 0.2 g of potassium iodide in 50 ml of ethyl methyl ketone is boiled under reflux for 18 hours under argon. The reaction mixture is then filtered and concentrated by evaporation. The residue is purified on silica gel (hexane/ethyl acetate 3:2) to give the title compound in the form of an oil; $^1$H-NMR, 200 MHz, CDCl$_3$, delta (ppm)=8.12 (d, 1H), 7.80 (dd, 1H), 7.5–7.7 (m, 4H), 7.25–7.35 (m, 2H), 7.05 (t, 1H), 5.30 (s, 2H), 4.35 (s, 2H), 3.90 (2s, 6H).

Example 18: 4-[3-(7-benzyloxy-2-quinolinylmethoxy)phenylamino]-2,2-diethyl-4-oxobutanoic acid Analogously to Example 3, the title compound is prepared starting from 3-(7-benzyloxy-2-quinolinylmethoxy)aniline and 2,2-diethylsuccinic acid. Slightly yellowish crystals of m.p. 89°–95° are obtained; IR (KBr): 3325, 2966, 1689, 1599, 1545, 1512, 1492, 1436, 1380, 1208, 1157, 1024, 842, 775, 695 cm$^{-1}$.

The starting materials are prepared as follows:

(a) 2-methyl-7-benzyloxyquinoline: Starting from 3-benzyloxy-aniline, the title compound is prepared analogously to Example 13(a) by reaction with crotonaldehyde and chloranil in 2-butanol [see also J. Heterocycl. Chem. 30 (1993) 17–21].

(b) 3-(7-benzyloxy-7-quinolinylmethoxy)aniline: Starting from 2-methyl-7-benzyloxyquinoline, the title compound is prepared analogously to Example 3(a) [NBS-bromination] and Example 3(b) [reaction with 3-aminophenol]; it is obtained in the form of yellowish crystals of m.p. 115°–117°.

Example 19: 4-[3-(7-hydroxy-2-quinolinylmethoxy)phenylamino]-2,2-diethyl-4-oxobutanoic acid A mixture consisting of 0.37 g of 4-[3-(7-benzyloxy-2-quinolinylmethoxy)phenylamino]-2,2-diethyl-4-oxobutanoic acid (Example 18), 2 ml of triethylamine, 0.0185 g of palladium/activated carbon catalyst and 10 ml of tetrahydrofuran is hydrogenated for 3 hours under normal pressure. The reaction mixture is then filtered and concentrated by evaporation. The residue is chromatographed on silica gel using methylene chloride/methanol 95:5 and 9:1. The title compound is obtained in the form of a slightly yellowish amorphous solid; $^1$H-NMR, 400 MHz, DMSO, delta (ppm)= 10.3 (s, 1H), 8.20 (d, 1H), 7.28 (m, 2H), 7.25 (d, 1H), 7.1–7.18 (m, 3H), 6.65 (dd, 1H), 5.22 (s, 2H), 2.47 (s, 2H), 1.49 (m, 4H), 0.78 (t, 6H).

Example 20: 4-[3-(7-bromo-2-quinolinylmethoxy)phenylamino]-2,2-diethyl-4-oxobutanoic acid 2 g of 3-(7-bromo-2-quinolinylmethoxy)aniline and 1.9 g of 2,2-diethylsuccinic acid anhydride (purified by distillation) are stirred in 28 ml of pyridine for 72 hours at 20° and concentrated by evaporation. The residue is suspended in 25 ml of 2N aqueous hydrochloric acid and the suspension is stirred for 30 min. at 20° and filtered. The precipitate is washed with water and crystallised from ethanol to give the title compound in the form of colourless crystals of m.p. 175°, IR (Nujol): inter alia 3600-2100, 3308, 1710, 1670, 1610, 1600, 1497 cm$^{-1}$.

The starting material is prepared as follows:

(a) 2-methyl-7-bromo-quinoline-1-oxide: A solution of 10.05 g of m-chloroperbenzoic acid in 75 ml of CH$_2$Cl$_2$ is added dropwise at 0°–10° in the course of 30 min. to a solution of 7.09 g of 2-methyl-7-bromo-quinoline [C. M. Leir, J. Org. Chem. 42(5) (1977) 911–913] in 75 ml of n-hexane and then the batch is stirred for 16 hours at 20°. It is then diluted with ethyl acetate, washed in succession with 2N aqueous solutions of K$_2$CO$_3$, Na$_2$S$_2$O$_3$ and NaCl, dried over Na$_2$SO$_4$ and concentrated by evaporation to give the title compound which is purified by crystallisation from CH$_2$Cl$_2$/ether/hexane.

(b) 2-chloromethyl-7-bromo-quinoline: A solution of 5.7 ml of benzene sulfochloride in 6.5 ml of toluene is added dropwise in the course of one hour, with stirring, at 50° to a solution of 5 g of 2-methyl-7-bromo-quinoline-1-oxide in 32 ml of toluene and the batch is then stirred for 16 hours at 50°. It is then taken up in ethyl acetate, washed with 2N aqueous solutions of NaHCO$_3$ and NaCl, dried over Na$_2$SO$_4$ and concentrated by evaporation. The evaporation residue is chromatographed on silica gel. The product-containing fractions eluted with toluene are combined and concentrated by evaporation to give the title compound which is further purified by crystallisation from CH$_2$Cl$_2$/ether/hexane.

(c) 3-(7-bromo-2-quinolinylmethoxy)aniline: 0.32 g of NaH (95%) is added at 0° to a solution of 1.38 g of 3-aminophenol in 30 ml of DMF and then the batch is stirred for 30 min. at 0°. 3.2 g of 2-chloromethyl-7-bromo-quinoline in solid form are then added thereto and the batch is stirred for a further one hour at 0° and for another hour at 20°. It is then diluted with ethyl acetate, washed with water, dried over Na$_2$SO$_4$ and concentrated by evaporation. The evaporation residue is chromatographed on 250 g of silica gel. The product-containing fractions eluted with toluene/ethyl acetate 95:5 are combined and concentrated by evaporation to give the title compound which is further purified by crystallisation from CH$_2$Cl$_2$/ether/hexane.

Example 21: 4-[3-(6,7-cyclopentano-2-quinolinylmethoxy)phenylamino]-2,2-diethyl-4-oxobutanoic acid 2.48 g of 3-(6,7-cyclopentano-2-quinolinylmethoxy)aniline and 2.67 g of 2,2-diethylsuccinic acid anhydride are stirred in 40 ml of pyridine for 72 hours at 20° and concentrated by evaporation. The residue is suspended in 25 ml of 2N aqueous hydrochloric acid and the suspension is stirred for 30 min. at 20° and filtered. The precipitate is washed with water and crystallised from ethanol to give the title compound in the form of colourless crystals of m.p. 180°, IR (KBr): inter alia 3600-2200, 3325, 1683, 1600, 1542 cm$^{-1}$.

The starting material is prepared as follows:

(a) 2-methyl-6,7-cyclopentano-quinoline-1-oxide: A solution of 19.9 g of m-chloroperbenzoic acid in 120 ml of CH$_2$Cl$_2$ is added dropwise at 0°–10° in the course of 30 min. to a solution of 11.6 g of 2-methyl-6,7-cyclopentano-quinoline [Lindner et al. Monatsh. Chem. 72 (1939) 354, 356] in 120 ml of CH$_2$Cl$_2$ and the batch is then stirred for 16 hours at 20°. It is then diluted with ethyl acetate, washed in succession with 2N aqueous solutions of K$_2$CO$_3$, Na$_2$S$_2$O$_3$ and NaCl, dried over Na$_2$SO$_4$ and concentrated by evaporation to give the title compound which is purified by crystallisation from CH$_2$Cl$_2$/ether.

(b) 2-chloromethyl-6,7-cyclopentano-quinoline: A solution of 9.47 ml of benzene sulfochloride in 12 ml of toluene is added dropwise in the course of one hour, with stirring, at 50° to a solution of 7.32 g of 2-methyl-6,7-cyclopentano-quinoline-1-oxide in 100 ml of toluene and then the batch is stirred for 16 hours at 50°. It is then taken up in ethyl acetate, washed with 2N aqueous solutions of NaHCO$_3$ and NaCl, dried over Na$_2$SO$_4$ and concentrated by evaporation. The evaporation residue is chromatographed on 250 g of silica gel. The product-containing fractions eluted with toluene and toluene/ethyl acetate 98:2 are combined and concentrated by evaporation to give the title compound which is further purified by crystallisation from CH$_2$Cl$_2$/ether.

(c) 3-(6,7-cyclopentano-2-quinolinylmethoxy)aniline: 0.313 g of NaH (95%) is added at 0° to a solution of 1.35 g of 3-aminophenol in 30 ml of DMF and then the batch is stirred for 30 min. at 0°. 2.66 g of 2-chloromethyl-6,7-cyclopentano-quinoline in solid form are then added and the batch is stirred for a further one hour at 0° and for another hour at 20°. It is then diluted with ethyl acetate, washed with water, dried over Na$_2$SO$_4$ and concentrated by evaporation. The evaporation residue is chromatographed on 100 g of silica gel. The product-containing fractions eluted with toluene/ethyl acetate 95:5 and 9:1 are combined and concentrated by evaporation to give the title compound which is further purified by crystallisation from CH$_2$Cl$_2$/ether/hexane.

Example 22: 4-[3-(7-trifluoromethoxy-2-quinolinylmethoxy)phenylamino]-2,2-diethyl-4-oxobutanoic acid 1.625 g of 3-(7-trifluoromethoxy-2-quinolinylmethoxy)aniline and 1.52 g of 2,2-diethylsuccinic acid anhydride are stirred in 26 ml of pyridine for 72 hours at 20° and concentrated by evaporation. The residue is suspended in 16 ml of 2N aqueous hydrochloric acid and the suspension is stirred for 30 min. at 20° and filtered. The precipitate is washed with water and crystallised from ethanol to give the title compound in the form of crystals of m.p. 172°, IR (KBr): inter alia 3620-2500, 3330, 1690, 1595, 1545 cm$^{-1}$.

The starting material is prepared as follows:

(a) 2-methyl-7-trifluoromethoxy-quinoline: 4.85 g of 3-trifluoromethoxyaniline are dissolved in 31.5 ml of 2-butanol; 11 ml of 4.8N HCl in 2-butanol and 6.22 g of 2,3-dichloro-1,4-naphthoquinone are added and the batch is heated to reflux temperature. A solution of 2.74 ml of crotonaldehyde in 6.5 ml of 2-butanol is then added dropwise in the course of 50 min. and then the batch is stirred for 20 min. at reflux temperature. It is then concentrated by evaporation, a further 35 ml of 2-butanol is added and the procedure of concentration by evaporation is repeated. The hydrochloride of the title compound is obtained in purified form by recrystallising the evaporation residue twice from methanol/tetrahydrofuran. In order to free the title compound, the above hydrochloride is suspended in water, rendered basic with 1N aqueous NaOH and the aqueous phase is extracted with ethyl acetate. The ethyl acetate phase is washed neutral with saturated aqueous NaCl solution, dried over $Na_2SO_4$ and concentrated by evaporation. The title compound obtained in the form of the evaporation residue is used in the next stage without being purified.

(b) 2-methyl-7-trifluoromethoxy-quinoline-1-oxide: A solution of 4.15 g of m-chloroperbenzoic acid in 30 ml of $CH_2Cl_2$ is added dropwise at 0°–10°, with stirring, in the course of 30 min. to a solution of 3 g of 2-methyl-7-trifluoromethoxy-quinoline in 30 ml of $CH_2Cl_2$ and then the batch is stirred for 16 hours at 20°. It is then diluted with ethyl acetate, washed in succession with 2N aqueous solutions of $K_2CO_3$, $Na_2S_2O_3$ and NaCl, dried over $Na_2SO_4$ and concentrated by evaporation to give the title compound which is purified by crystallisation from $CH_2Cl_2$/ether.

(c) 2-chloromethyl-7-trifluoromethoxy-quinoline: 2.68 ml of benzene sulfochloride in 3.5 ml of toluene are added dropwise in the course of one hour, with stirring, at 50° to a solution of 2.53 g of 2-methyl-7-trifluoromethoxy-quinoline-1-oxide in 35 ml of toluene and then the batch is stirred for 16 hours at 50°. It is then taken up in ethyl acetate, washed with 2N aqueous solutions of $NaHCO_3$ and NaCl, dried over $Na_2SO_4$ and concentrated by evaporation. The evaporation residue is chromatographed on silica gel (100 g). The product-containing fractions eluted with toluene are combined and concentrated by evaporation to give the title compound which is further processed directly.

(d) 3-(7-trifluoromethoxy-2-quinolinylmethoxy)aniline: 0.175 g of NaH (95%) is added at 0° to a solution of 0.754 g of 3-aminophenol in 20 ml of DMF and then the batch is stirred for 30 min. at 0°. 1.78 g of 2-chloromethyl-7-trifluoromethoxy-quinoline in solid form are then added and the batch is stirred for a further one hour at 0° and for another hour at 20°. It is then diluted with ethyl acetate, washed with water, dried over $Na_2SO_4$ and concentrated by evaporation. The evaporation residue is chromatographed on 100 g of silica gel. The product-containing fractions eluted with toluene/ethyl acetate 98:2 and 95:5 are combined and concentrated by evaporation to give the title compound which is further purified by crystallisation from $CH_2Cl_2$/ether/hexane.

Example 23: 4-[3-(7-acetyl-2-quinolinylmethoxy)phenylamino]-2,2-diethyl-4-oxobutanoic acid 0.36 g of 3-(7-acetyl-2-quinolinylmethoxy)aniline and 0.385 g of 2,2-diethylsuccinic acid anhydride are stirred in 5 ml of pyridine for 72 hours at 20° and concentrated by evaporation. The residue is suspended in 5 ml of 2N aqueous hydrochloric acid, the suspension is stirred for 30 min. at 20° and filtered and the residue retained on the filter is dried in vacuo at 20°. The crude product obtained is chromatographed on 50 g of silica gel. The product-containing fractions (eluted with toluene/ethyl acetate 1:1 and with ethyl acetate) are combined and concentrated by evaporation and the evaporation residue is recrystallised from a $CH_2Cl_2$/methanol/acetone mixture to give the title compound in the form of crystals of m.p. 164°. IR (Nujol): inter alia 3600-2100, 3350, 1675, 1600 cm$^{-1}$.

The starting material is prepared as follows:

(a) 2-methyl-7-acetyl-quinoline: 13.5 g of 3-amino-acetophenone are dissolved in 115 ml of 2-butanol; 40 ml of 4.8N HCl in 2-butanol and 22.7 g of 2,3-dichloro-1,4-naphthoquinone are added and the batch is heated to reflux temperature. A solution of 10 ml of crotonaldehyde in 24 ml of 2-butanol is then added dropwise in the course of 50 min. and then the batch is stirred at reflux temperature for 20 min. It is then concentrated to dryness by evaporation, the evaporation residue is dissolved in ethyl acetate, washed with 1N aqueous solutions of NaOH and NaCl, dried over $Na_2SO_4$ and concentrated by evaporation to give the crude title compound which is further processed directly.

(b) 2-methyl-7-acetyl-quinoline-1-oxide: A solution of 5 g of m-chloroperbenzoic acid in 50 ml of $CH_2Cl_2$ is added dropwise at 0°–10°, with stirring, in the course of 30 min. to a solution of 4.2 g of crude 2-methyl-7-acetyl-quinoline in 30 ml of $CH_2Cl_2$ and then the batch is stirred for 16 hours at 20°. It is then diluted with ethyl acetate, washed in succession with 2N aqueous solutions of $K_2CO_3$, $Na_2S_2O_3$ and NaCl, dried over $Na_2SO_4$ and concentrated by evaporation. The evaporation residue is chromatographed on 100 g of silica gel. The product-containing fractions eluted with ethyl acetate and ethyl acetate/methanol 95:5 are combined and concentrated by evaporation to give the title compound which is further purified by crystallisation from $CH_2Cl_2$/ether/hexane.

(c) 2-chloromethyl-7-acetyl-quinoline: 1.07 ml of benzene sulfochloride in 2 ml of toluene are added dropwise, with stirring, at 50° in the course of one hour to a solution of 0.8 g of 2-methyl-7-acetyl-quinoline-1-oxide in 15 ml of toluene and then the batch is stirred for 16 hours at 50°. It is then taken up in ethyl acetate, washed with 2N aqueous solutions of $NaHCO_3$ and NaCl, dried over $Na_2SO_4$ and concentrated by evaporation. The evaporation residue is chromatographed on 100 g of silica gel. The product-containing fractions eluted with toluene/ethyl acetate 9:1 are combined and concentrated by evaporation to give the title compound which is further purified by crystallisation from $CH_2Cl_2$/ether/hexane.

(d) 3-(7-acetyl-2-quinolinylmethoxy)aniline: 30 mg of NaH (95%) are added at 0° to a solution of 0.13 g of 3-aminophenol in 2.5 ml of DMF and then the batch is stirred for 30 min. at 0°. 0.25 g of 2-chloromethyl-7-acetyl-quinoline in solid form is then added and the batch is stirred for a further one hour at 0° and for another hour at 20°. It is then diluted with ethyl acetate, washed with water, dried over $Na_2SO_4$ and concentrated by evaporation. The evaporation residue is chromatographed on 25 g of silica gel. The product-containing fractions eluted with toluene/ethyl acetate 85:15 are combined and concentrated by evaporation to give the title compound which is further reacted directly.

Example 24: 4-[3-(6-methyl-2-quinolinylmethoxy)phenylamino]-2,2-diethyl-4-oxobutanoic acid 2.05 g of 3-(6-methyl-2-quinolinylmethoxy)aniline and 2.42 g of 2,2-diethylsuccinic acid anhydride are stirred in 30 ml of pyridine for 72 hours at 20° and concentrated by evaporation. The residue is suspended in 25 ml of 2N aqueous hydrochloric acid and the suspension is stirred for 30 min. at 20° and filtered. The precipitate is washed with water and crystallised from ethanol to give the title compound in the form of crystals of m.p. 175°, IR (Nujol): inter alia 3600-2600, 3320, 1685, 1545 cm$^{-1}$.

The starting material is prepared as follows:

(a) 3-(6-methyl-2-quinolinylmethoxy)aniline: 0.43 g of NaH (95%) is added at 0° to a solution of 1.85 g of 3-aminophenol in 30 ml of DMF and then the batch is stirred for 30 min. at 0°. 3.2 g of 2-chloromethyl-6-methyl-quinoline [see C.A. 82, 57733p and U.S. Pat. No. 3,829,573] in solid form are then added and the batch is stirred for a further one hour at 0° and for another hour at 20°. It is then diluted with ethyl acetate, washed with water, dried over $Na_2SO_4$ and concentrated by evaporation. The evaporation residue is chromatographed on 250 g of silica gel. The product-containing fractions eluted with toluene/ethyl acetate 95:5 and 9:1 are combined and concentrated by evaporation to give the title compound which is further purified by being crystallised twice from $CH_2Cl_2$/ether/hexane.

Example 25: 4-[3-(6,7-dimethyl-2-quinolinylmethoxy)phenylamino]-2,2-diethyl-4-oxobutanoic acid 1.65 g of 3-(6,7-dimethyl-2-quinolinylmethoxy)aniline and 1.85 g of 2,2-diethylsuccinic acid anhydride are stirred in 25 ml of pyridine for 72 hours at 20° and concentrated by evaporation. The residue is suspended in 25 ml of 2N aqueous hydrochloric acid and the suspension is stirred for 30 min. at 20° and filtered. The precipitate is washed with water and crystallised from ethanol to give the title compound in the form of crystals of m.p. 184°, IR (KBr): inter alia 3600-2500, 3320, 1680, 1600, 1547 cm$^{-1}$.

The starting material is prepared as follows:

(a) 2,6,7-trimethyl-quinoline-1-oxide: A solution of 15.8 g of to-chloroperbenzoic acid in 80 ml of $CH_2Cl_2$ is added dropwise at 0°–10° in the course of 30 min. to a solution of 8.6 g of 2,6,7-trimethyl-quinoline [A. G. Osborn, Tetrahedron 39(17) (1983) 2831–2841] in 80 ml of $CH_2Cl_2$ and then the batch is stirred for 16 hours at 20°. It is then diluted with ethyl acetate, washed in succession with 2N aqueous solutions of $K_2CO_3$, $Na_2S_2O_3$ and NaCl, dried over $Na_2SO_4$ and concentrated by evaporation to give the title compound which is further purified by crystallisation from $CH_2Cl_2$/ether/hexane.

(b) 2-chloromethyl-6,7-dimethyl-quinoline: A solution of 9.4 ml of benzene sulfochloride in 10 ml of toluene is added dropwise, with stirring, at 50° in the course of one hour to a solution of 6.35 g of 2,6,7-trimethyl-quinoline-1-oxide in 50 ml of toluene and then the batch is stirred for 16 hours at 50°. It is then taken up in ethyl acetate, washed with 2N aqueous solutions of $NaHCO_3$ and NaCl, dried over $Na_2SO_4$ and concentrated by evaporation. The evaporation residue is chromatographed on 250 g of silica gel. The product-containing fractions eluted with toluene and toluene/ethyl acetate 99:1 are combined and concentrated by evaporation to give the title compound which is further purified by crystallisation from $CH_2Cl_2$/ether/hexane.

(c) 3-(6,7-dimethyl-2-quinolinylmethoxy)aniline: 0.35 g of NaH (95%) is added at 0° to a solution of 1.51 g of 3-aminophenol in 30 ml of DMF and then the batch is stirred for 30 min. at 0°. 2.8 g of 2-chloromethyl-6,7-dimethyl-quinoline in solid form are then added and the batch is stirred for a further one hour at 0° and for another hour at 20°. It is then diluted with ethyl acetate, washed with water, dried over $Na_2SO_4$ and concentrated by evaporation. The evaporation residue is chromatographed on 250 g of silica gel. The product-containing fractions eluted with toluene/ethyl acetate 95:5 and 9:1 are combined and concentrated by evaporation to give the title compound which is further purified by crystallisation from $CH_2Cl_2$/ether.

Example 26: 4-[3-(7-methyl-2-quinolinylmethoxy)phenylamino]-2,2-diethyl-4-oxobutanoic acid The title compound is prepared analogously to the compound described in Example 20 from 2,2-diethylsuccinic acid anhydride and 3-(7-methyl-2-quinolinylmethoxy)aniline; colourless crystals of m.p. 162°–163°.

The starting materials are prepared as follows:

(a) 2,7-dimethyl-quinoline-1-oxide: The title compound is prepared analogously to Example 20(a) from 2,7-dimethylquinoline [Z. Song et al., J. Heterocyclic Chem. 30 (1993) 17–21]; light brown crystals of m.p. 65°–66°.

(b) 2-chloromethyl-7-methyl-quinoline: The title compound is prepared analogously to Example 20(b) from 2,7-dimethyl-quinoline-1 -oxide; colourless crystals of m.p. 75°–76°.

(c) 3-(7-methyl-2-quinolinylmethoxy)aniline: The title compound is prepared analogously to Example 20(c) from 2-chloromethyl-7-methyl-quinoline and 3-aminophenol; beige crystals of m.p. 97°–98°.

Example 27: 4-[3-(7-methoxy-2-quinolinylmethoxy)phenylamino]-2,2-diethyl-4-oxobutanoic acid The title compound is prepared analogously to the compound described in Example 20 from 2,2-diethylsuccinic acid anhydride and 3-(7-methoxy-2-quinolinylmethoxy)aniline; colourless crystals of m.p. 163°–164°.

The starting materials are prepared as follows:

(a) 2-methyl-7-methoxy-quinoline-1-oxide: The title compound is prepared analogously to Example 20(a) from 2-methyl-7-methoxy-quinoline [Z. Song et al., J. Heterocyclic Chem. 30 (1993) 17–21]; beige crystals of m.p. 103°–104°.

(b) 2-chloromethyl-7-methoxy-quinoline: The title compound is prepared analogously to Example 20(b) from 2-methyl-7-methoxy-quinoline-1-oxide; colourless crystals of m.p. 64°–65°.

(c) 3-(7methoxy-2-quinolinylmethoxy)aniline: The title compound is prepared analogously to Example 20(c) from 2-chloromethyl-7-methoxy-quinoline and 3-aminophenol; beige crystals of m.p. 96°–97°.

Example 28: 4-[3-(7-fluoro-2-quinolinylmethoxy)phenylamino]-2,2-dimethyl-4-oxobutanoic acid The title compound is prepared analogously to the compound described in Example 20 from 2,2-dimethylsuccinic acid anhydride and 3-(7-fluoro-2-quinolinylmethoxy)aniline; colourless crystals of m.p. 209°–210°.

Example 29: 4-[3-(7-fluoro-2-quinolinylmethoxy)phenylamino]-2-ethyl-2-methyl-4-oxobutanoic acid The title compound is prepared analogously to the compound described in Example 20 from 2-ethyl-2-methylsuccinic acid anhydride and 3-(7-fluoro-2-quinolinylmethoxy)aniline; colourless crystals of m.p. 179°–180°.

Example 30: 1-[3-(7-fluoro-2-quinolinylmethoxy)phenylaminocarbonylmethyl]-cyclopentanecarboxylic acid The title compound is prepared analogously to the compound described in Example 20 from (1-carboxycyclopentyl)acetic acid anhydride (obtained from the acid by means of acetyl chloride analogously to Example 1) and 3-(7-fluoro-2-quinolinylmethoxy)aniline; beige crystals of m.p. 187°–188°.

Example 31: 1-[3-(7-fluoro-2-quinolinylmethoxy)phenylaminocarbonylmethyl]-cyclohexanecarboxylic acid The title compound is prepared analogously to the compound described in Example 20 from (1-carboxycyclohexyl)acetic acid anhydride (obtained from the acid by means of acetyl chloride analogously to Example 1) and 3-(7-fluoro-2-quinolinylmethoxy)aniline; colourless crystals of m.p. 190°–191°.

Example 32: 4-[3-(7-fluoro-2-quinolinylmethoxy)phenylamino]-2,2-dipropyl-4-oxobutanoic acid The title compound is prepared analogously to the compound described in Example 20 from 2,2-dipropylsuccinic acid anhydride and 3-(7-fluoro-2-quinolinylmethoxy)aniline; beige crystals of m.p. 155°–156°.

Example 33: 4-[3-(7-fluoro-2-quinolinylmethoxy)phenylamino]-2,2-dibutyl-4-oxobutanoic acid The title compound is prepared analogously to the compound described in Example 20 from 2,2-dibutylsuccinic acid anhydride (prepared analogously to the instructions of H. Le Moal et al. Bull. Soc. Chim. 1964, 579 and 828) and 3-(7-fluoro-2-quinolinylmethoxy)aniline; beige crystals of m.p. 156°–157°.

Example 34: 4-[3-(7-fluoro-2-quinolinylmethoxy)phenylamino]-2,2-diethyl-4-oxobutanoic acid The title compound is prepared analogously to the compound described in Example 20 from 2,2-diethylsuccinic acid anhydride and 3-(7-fluoro-2-quinolinylmethoxy)aniline; colourless crystals of m.p. 166°–167°.

The starting materials are prepared as follows:

(a) 2-methyl-7-fluoro-quinoline-1-oxide: The title compound is prepared analogously to Example 20(a) from 2-methyl-7-fluoro-quinoline [Z. Song et al., J. Heterocyclic Chem. 30 (1993) 17–21]; beige crystals of m.p. 82°–83°.

(b) 2-chloromethyl-7-fluoro-quinoline: The title compound is prepared analogously to Example 20(b) from 2-methyl-7-fluoro-quinoline-1-oxide; beige crystals of m.p. 70°–71°.

(c) 3-(7-fluoro-2-quinolinylmethoxy)aniline: The title compound is prepared analogously to Example 20(c) from 2-chloromethyl-7-fluoro-quinoline and 3-aminophenol; beige crystals of m.p. 92°–93°.

Example 35: Sodium salt of 4-[3-(7-fluoro-2-quinolinylmethoxy)phenylamino]-2,2-diethyl-4-oxobutanoic acid (1.4 $H_2O$)

17.65 g of 4-[3-(7-fluoro-2-quinolinylmethoxy)phenylamino]-2,2-diethyl-4-oxobutanoic acid are dissolved in 200 ml of tetrahydrofuran, and 20.8 ml of an aqueous 2N sodium hydroxide solution are added. The solution is concentrated by evaporation, suspended in dichloromethane and concentrated by evaporation again. The residue is stirred under reflux with 200 ml of dichloromethane for 15 min. and cooled and the mixture is filtered with suction to give the title compound in the form of a colourless powder of m.p. 118°–120°.

Example 36: Potassium salt of 4-[3-(7-fluoro-2-quinolinylmethoxy)phenylamino]-2,2-diethyl-4-oxobutanoic acid (2.6 $H_2O$)

17.65 g of 4-[3-(7-fluoro-2-quinolinylmethoxy)phenylamino]-2,2-diethyl-4-oxobutanoic acid are dissolved in 200 ml of tetrahydrofuran, and 20.8 ml of an aqueous 2N potassium hydroxide solution are added. The solution is concentrated by evaporation, suspended in dichloromethane and concentrated by evaporation again. The residue is stirred under reflux with 200 ml of dichloromethane for 15 min. and cooled and the mixture is filtered with suction to give the title compound in the form of a colourless powder of m.p. 114°–116°.

Examples A to G: Pharmaceutical Compositions

The term "active ingredient" is to be understood hereinafter as meaning a compound (I), in free form or in the form of a pharmaceutically acceptable salt, especially such a compound that is described as a product in one of the preceding Examples.

Example A: An inhalation suspension that comprises propellants, forms a solid aerosol and comprises 0.1% by weight active ingredient:

| Composition | % by weight |
| --- | --- |
| active ingredient, micronised | 0.1 |
| sorbitan trioleate | 0.5 |
| propellant A (trichlorotrifluoroethane) | 4.4 |
| propellant B (dichlorodifluoromethane and 1,2-dichlorotetrafluoroethane) | 15.0<br>80.0 |

With the exclusion of moisture, the active ingredient is suspended, with the aid of a customary homogeniser, in the trichlorotrifluoroethane with the addition of the sorbitan trioleate, and the suspension is introduced into an aerosol container provided with a metering valve. The container is closed and filled up with propellant B under pressure.

Example B: An approximately 2%, aqueous solution of the active ingredient, in the form of its sodium or potassium salt, suitable for inhalation:

| Composition | |
| --- | --- |
| active ingredient (K or Na salt) | 2000 mg |
| disodium salt of ethylenediaminetetraacetic acid | 10 mg |
| benzalkonium chloride | 10 mg |
| water, freshly distilled | ad 100 ml |
| propellant | as required |

The active ingredient is dissolved in approximately 60 ml of freshly distilled water, and the stabiliser (disodium salt of ethylenediaminetetraacetic acid) and the preservative (benzalkonium chloride) are added. When all of the components have dissolved completely, the resulting solution is made up to 100 ml and introduced into small pressurised bottles. The bottles are closed in gas-tight manner. The propellant is added, as required, in gaseous form under pressure or in liquid form.

Example C: An ointment, comprising 0.05% by weight active ingredient:

| Composition | % by weight |
| --- | --- |
| active ingredient | 0.05 |
| vaseline | 45.00 |
| paraffin oil | 19.60 |
| cetyl alcohol | 5.00 |
| beeswax | 5.00 |
| sorbitan sesquioleate | 5.00 |
| p-hydroxybenzoic acid ester | 0.20 |
| water, demineralised | 20.15 |

The fatty substances and emulsifiers are melted together. The preservative is dissolved in water and the solution is incorporated into the fatty melt at elevated temperature by emulsification. After cooling, a suspension of the active ingredient in part of the fatty melt is incorporated into the emulsion.

Example D: Tablets, each comprising 50 mg of active ingredient:

| Composition (10 000 tablets) | |
| --- | --- |
| active ingredient | 500.0 g |
| lactose | 500.0 g |
| potato starch | 352.0 g |

| Composition (10 000 tablets) | |
|---|---|
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of the potato starch and the mixture is moistened with an ethanolic solution of the gelatin and granulated through a sieve. After drying, the remainder of the potato starch, the magnesium stearate, the talc and the silica are admixed and the mixture is compressed to form tablets each weighing 145 mg and each comprising 50 mg of active ingredient, which may, if desired, be provided with dividing notches for finer adaptation of the dose.

Example E: Film-coated tablets, each comprising 100 mg of active ingredient:

| Composition (1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed. The mixture is moistened with a paste, produced from 15 g of corn starch and water (with heating), and granulated. The granules are dried and the remainder of the corn starch, the talc and the calcium stearate are mixed with the granules. The mixture is compressed to form tablets (weight: each 280 mg) and the tablets are coated with a solution of the hydroxypropylmethylcellulose and the shellac in dichloromethane (final weight of each film-coated tablet: 283 mg).

Example F: Hard gelatin capsules, each comprising 100 mg of active ingredient:

| Composition (1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm onto the lyophilised active ingredient. The two components are intimately mixed. Then first the lactose is added through a sieve having a mesh size of 0.6 mm and then the microcrystalline cellulose is added through a sieve having a mesh size of 0.9 mm. All four components are then intimately mixed for 10 minutes. Finally, the magnesium stearate is added through a sieve having a mesh size of 0.8 mm. After further mixing (3 minutes), 390 mg portions of the resulting formulation are introduced into size 0 hard gelatin capsules.

Example G: An injection or infusion solution, comprising 5 mg of active ingredient per 2.5 ml-ampoule:

| Composition (1000 ampoules) | |
|---|---|
| active ingredient | 5.0 g |
| sodium chloride | 22.5 g |
| phosphate buffer solution (pH: 7.4) | 300.0 g |
| demineralised water | ad 2500.0 ml |

The active ingredient and the sodium chloride are dissolved in 1000 ml of demineralised water. The solution is filtered through a microfilter. The phosphate buffer solution is added to the filtrate and the mixture is made up to 2500 ml with demineralised water. In order to prepare unit dose forms, 2.5 ml portions of the mixture are introduced into glass ampoules, which then each comprise 5 mg of active ingredient.

What is claimed is:

1. A compound of formula I,

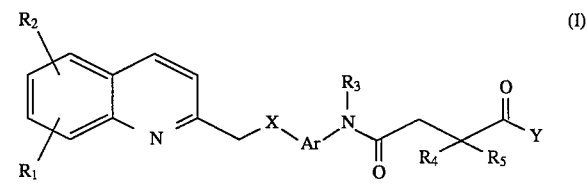

wherein $R_1$ and $R_2$ are each independently of the other hydrogen, lower alkyl, halo-lower alkyl, aryl-lower alkyl, cycloalkyl, halogen, hydroxy, lower alkoxy, halo-lower alkoxy, aryl-lower alkoxy, acyloxy, mercapto, lower alkyl(-thio, -sulfinyl or -sulfonyl), amino, lower alkylamino, di-lower alkylamino, acylamino, nitro, acyl, carboxy, lower alkoxycarbonyl, aminocarbonyl, N-lower alkylaminocarbonyl, N,N-di-lower alkylaminocarbonyl or cyano, or $R_1$ and $R_2$ together form —$(CH_2)_m$—, wherein m is 3, 4 or 5, $R_3$ is hydrogen, lower alkyl, (carboxy-, lower alkoxycarbonyl-, aminocarbonyl-, N-lower alkylaminocarbonyl-, N,N-di-lower alkylaminocarbonyl- or cyano-)lower alkyl, phenyl-lower alkyl; (carboxy-, lower alkoxycarbonyl-, aminocarbonyl-, N-lower alkylaminocarbonyl-, N,N-di-lower alkylaminocarbonyl- or cyano-)phenyl-lower alkyl, which may be additionally substituted in the phenyl ring by lower alkoxy; or lower alkyl that is substituted by the group —$NHSO_2R$, wherein R is lower alkyl, halo-lower alkyl or aryl, $R_4$ and $R_5$ are each independently of the other lower alkyl, or $R_4$ and $R_5$ together form —$(CH_2)_n$—, wherein n is 3, 4, 5 or 6, X is O, S, SO or $SO_2$, Ar is 1,3-phenylene or 2,7-naphthylene, and Y is hydroxy, lower alkoxy, amino, lower alkylamino or di-lower alkylamino; or a salt thereof.

2. A compound of formula I according to claim 1, wherein $R_1$ and $R_2$ are each independently of the other hydrogen, lower alkyl, halo-lower alkyl, phenyl-lower alkyl, halogen, hydroxy, lower alkoxy, halo-lower alkoxy, phenyl-lower alkoxy, lower alkyl(-thio, -sulfinyl or -sulfonyl), nitro, lower alkanoyl or cyano, or $R_1$ and $R_2$ together form —$(CH_2)_3$— or —$(CH_2)_4$—, $R_3$ is hydrogen, lower alkyl, carboxy-lower alkyl, lower alkoxycarbonyl-lower alkyl, N,N-di-lower alkylaminocarbonyl-lower alkyl; (carboxy- or lower alkoxycarbonyl-)-phenyl-lower alkyl, which may be additionally substituted in the phenyl ring by lower alkoxy; or lower alkyl that is substituted by the group —NHSO$_2$R, wherein R is lower alkyl, trifluoromethyl, phenyl, lower alkyl-phenyl or lower alkenyloxy-phenyl, $R_4$ and $R_5$ are each independently of the other lower alkyl, or $R_4$ and $R_5$ together form —(CH$_2$)$_4$— or —(CH$_2$)$_5$—, X is O, S, SO or SO$_2$, Ar is 1,3-phenylene or 2,7-naphthylene, and Y is hydroxy, lower alkoxy, amino, lower alkylamino or di-lower alkylamino; or a salt thereof.

3. A compound of formula I according to claim 1, wherein $R_1$ and $R_2$ are each independently of the other hydrogen, lower alkyl, trifluoromethyl, halogen, lower alkoxy, lower alkyl(-thio, -sulfinyl or -sulfonyl), nitro or cyano, $R_3$ is hydrogen, lower alkyl, carboxy-lower alkyl, lower alkoxycarbonyl-lower alkyl, N,N-di-lower alkylaminocarbonyl-lower alkyl or (carboxy- or lower alkoxycarbonyl-)-phenyl-lower alkyl, $R_4$ and $R_5$ are each independently of the other lower alkyl, or $R_4$ and $R_5$ together form —(CH$_2$)$_4$— or —(CH$_2$)$_5$—, X is O, S, SO or SO$_2$, Ar is 1,3-phenylene or 2,7-naphthylene, and Y is hydroxy, lower alkoxy, amino, lower alkylamino or di-lower alkylamino; or a salt thereof.

4. A compound of formula I according to claim 1, wherein $R_1$ and $R_2$ are each independently of the other hydrogen, lower alkyl, trifluoromethyl, halogen, lower alkoxy, lower alkylthio, nitro or cyano, $R_3$ is hydrogen, lower alkyl, carboxy-lower alkyl or carboxyphenyl-lower alkyl, $R_4$ and $R_5$ are each independently of the other lower alkyl, or $R_4$ and $R_5$ together form —(CH$_2$)$_4$— or —(CH$_2$)$_5$—, X is O, S, SO or SO$_2$, Ar is 1,3-phenylene or 2,7-naphthylene, and Y is hydroxy, lower alkoxy or amino, or a pharmaceutically acceptable salt thereof.

5. A compound of formula I according to claim 1, wherein $R_1$ is hydrogen, lower alkyl, trifluoromethyl, halogen, lower alkoxy, lower alkylthio, nitro or cyano, $R_2$ and $R_3$ are hydrogen, $R_4$ and $R_5$ are each independently of the other C$_1$–C$_3$alkyl, or $R_4$ and $R_5$ together form —(CH$_2$)$_4$— or —(CH$_2$)$_5$—, X is O or S, Ar is 1,3-phenylene or 2,7-naphthylene, and Y is hydroxy, or a pharmaceutically acceptable salt thereof.

6. A compound according to claim 1 of formula Ia

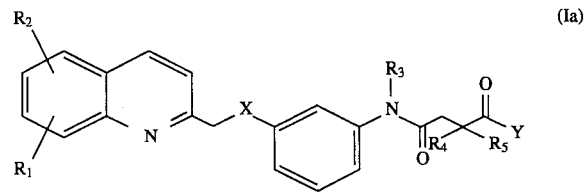

wherein $R_1$ and $R_2$ are each independently of the other hydrogen, chlorine or fluorine, $R_3$ is hydrogen, $R_4$ and $R_5$ are ethyl, X is O, and Y is hydroxy, lower alkoxy or amino, or a pharmaceutically acceptable salt thereof.

7. A compound according to claim 6 of formula Ia, wherein $R_1$ is hydrogen, chlorine or fluorine, $R_2$ is hydrogen or fluorine, $R_3$ is hydrogen, $R_4$ and $R_5$ are ethyl, X is O, and Y is hydroxy, or a pharmaceutically acceptable salt thereof.

8. 4-[3-(2-quinolinylmethoxy)phenylamino]-2,2-diethyl-4-oxobutanoic acid according to claim 1, or a pharmaceutically acceptable salt thereof.

9. 4-[3-(7-fluoro-2-quinolinylmethoxy)phenylamino]-2,2-diethyl-4-oxobutanoic acid according to claim 1, or a pharmaceutically acceptable salt thereof.

10. 4-[3-(7-trifluoromethyl-2-quinolinylmethoxy)phenylamino]-2,2-diethyl-4-oxobutanoic acid according to claim 1, or a pharmaceutically acceptable salt thereof.

11. A pharmaceutical composition comprising a compound according to claim 1 and at least one pharmaceutically acceptable carrier.

12. A pharmaceutical composition comprising a compound according to claim 9 and at least one pharmaceutically acceptable carrier.

13. A compound according to claim 1 for use in the treatment of disorders responsive to inhibition of leukotrienes.

* * * * *